(12) United States Patent
Nabki et al.

(10) Patent No.: US 11,908,554 B2
(45) Date of Patent: Feb. 20, 2024

(54) ULTRA WIDEBAND (UWB) TRANSMITTER AND RECEIVER CIRCUITS

(71) Applicants: Frederic Nabki, Montreal (CA); Dominic Deslandes, Montreal (CA); Michiel Soer, Montreal (CA); Gabriel Morin-Laporte, Montreal (CA); Mohammad Taherzadeh-Sani, Montreal (CA)

(72) Inventors: Frederic Nabki, Montreal (CA); Dominic Deslandes, Montreal (CA); Michiel Soer, Montreal (CA); Gabriel Morin-Laporte, Montreal (CA); Mohammad Taherzadeh-Sani, Montreal (CA)

( * ) Notice: Subject to any disclaimer, the term of this patent is extended or adjusted under 35 U.S.C. 154(b) by 85 days.

(21) Appl. No.: 17/593,317

(22) PCT Filed: Mar. 18, 2020

(86) PCT No.: PCT/CA2020/000030
§ 371 (c)(1),
(2) Date: Sep. 15, 2021

(87) PCT Pub. No.: WO2020/186333
PCT Pub. Date: Sep. 24, 2020

(65) Prior Publication Data
US 2022/0173761 A1 Jun. 2, 2022

Related U.S. Application Data

(60) Provisional application No. 62/819,847, filed on Mar. 18, 2019.

(51) Int. Cl.
*H04B 1/40* (2015.01)
*H03F 1/02* (2006.01)
(Continued)

(52) U.S. Cl.
CPC ............ *G16H 10/60* (2018.01); *G16H 40/20* (2018.01); *G16H 40/67* (2018.01); *H03F 1/02* (2013.01);
(Continued)

(58) Field of Classification Search
None
See application file for complete search history.

(56) References Cited

U.S. PATENT DOCUMENTS 6,088,602 A 7/2000 Banister
6,667,642 B1 12/2003 Moyal
(Continued)

*Primary Examiner* — Pablo N Tran
(74) *Attorney, Agent, or Firm* — Rosenberg, Klein & Lee

(57) ABSTRACT

Ultra-Wideband (UWB) wireless technology transmits digital data as modulated coded impulses over a very wide frequency spectrum with very low power over a short distance. To support extended operation, particularly with battery power sources, the inventors have established UWB devices which support wake-up from deep sleep modes when these devices exploit low frequency clock sources for ultra-low power consumption. Further, power consumption may be reduced by exploiting transistors or so-called compounded MOSFET structures whose effective gain and output resistance exceeds any single transistor irrespective of length or by employing biasless low power differential (exponential) transconductance stages within operational transconductance amplifiers in order to provide very high gain low power amplification stages. Further, the inventors have established voltage reference sources that consume very low current, a few nA, and ultra-low power low dropout regulators.

9 Claims, 24 Drawing Sheets

(51) Int. Cl.
　　　*H04W 52/02*　　(2009.01)
　　　*H03F 3/24*　　(2006.01)
　　　*G16H 10/60*　　(2018.01)
　　　*G16H 40/20*　　(2018.01)
　　　*G16H 40/67*　　(2018.01)

(52) U.S. Cl.
　　　CPC ................. *H03F 3/24* (2013.01); *H04B 1/40* (2013.01); *H04W 52/029* (2013.01)

(56) References Cited

U.S. PATENT DOCUMENTS

| | | | |
|---|---|---|---|
| 2009/0004981 A1* | 1/2009 | Eliezer | H03F 1/3247 455/127.1 |
| 2011/0207420 A1* | 8/2011 | Rajendran | H03F 3/195 455/127.1 |
| 2016/0043761 A1* | 2/2016 | Kim | H03F 1/3223 375/346 |

* cited by examiner

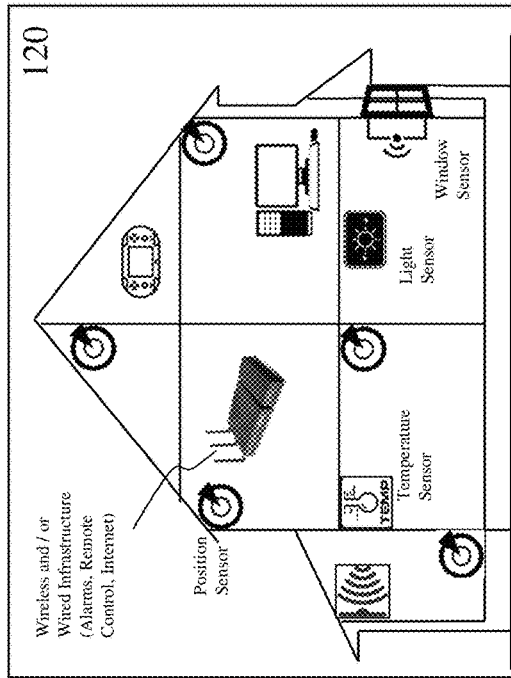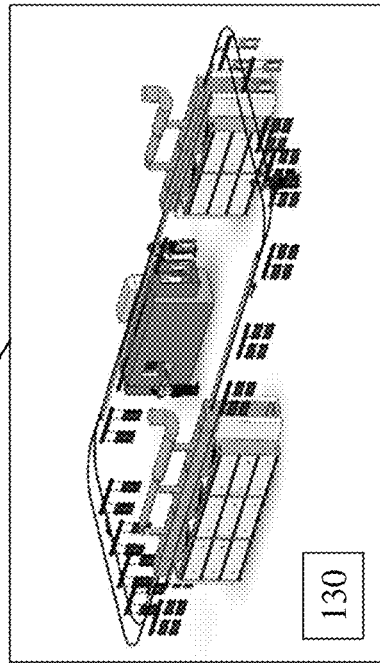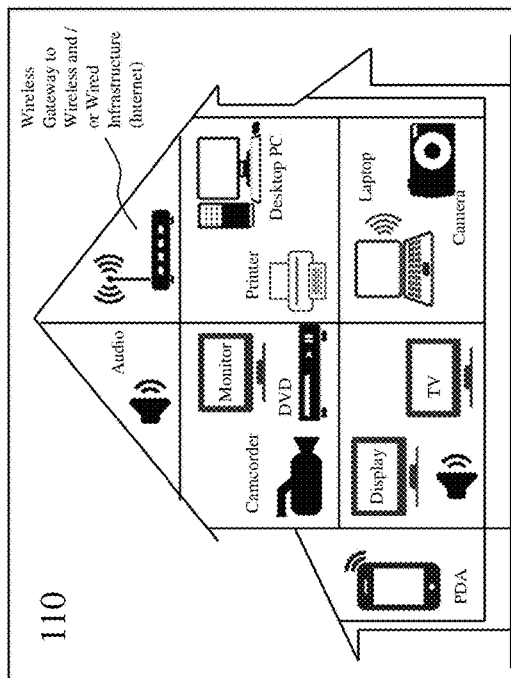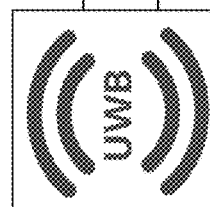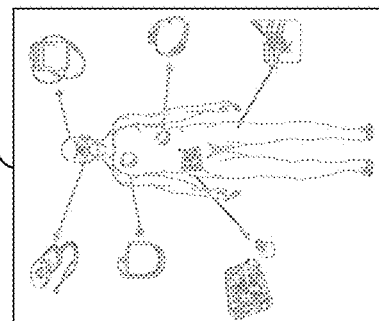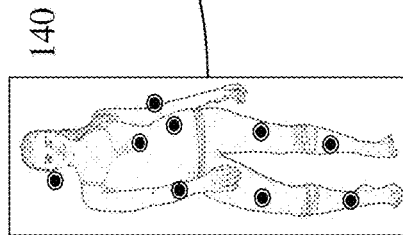
Figure 1

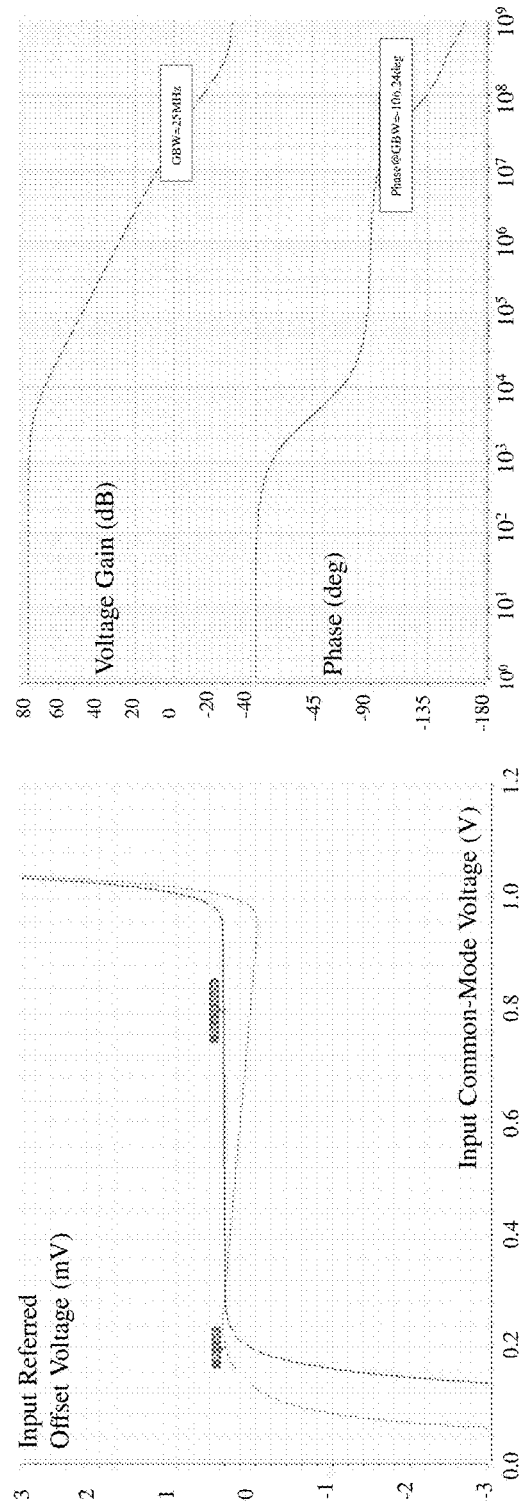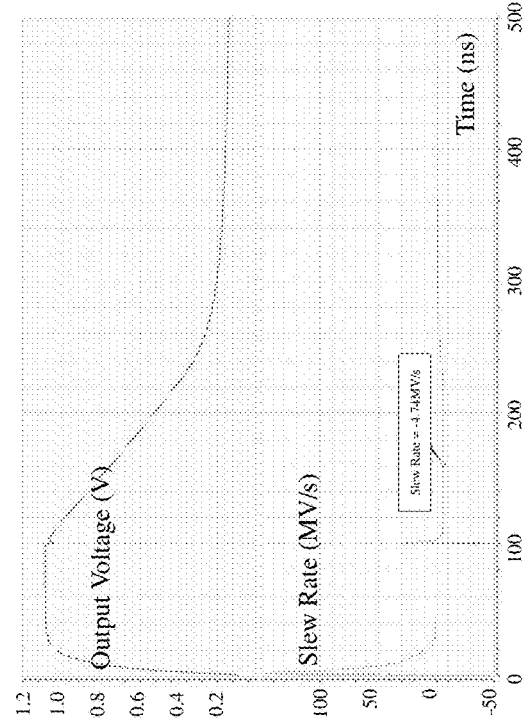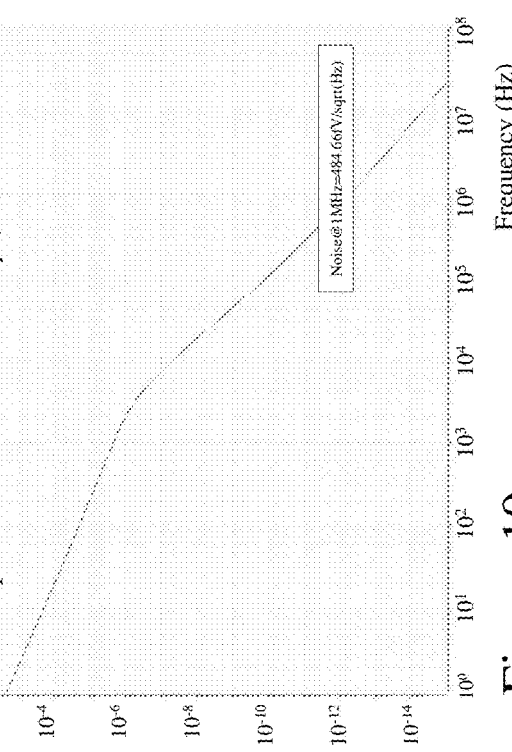
Figure 17
Figure 18
Figure 19
Figure 20

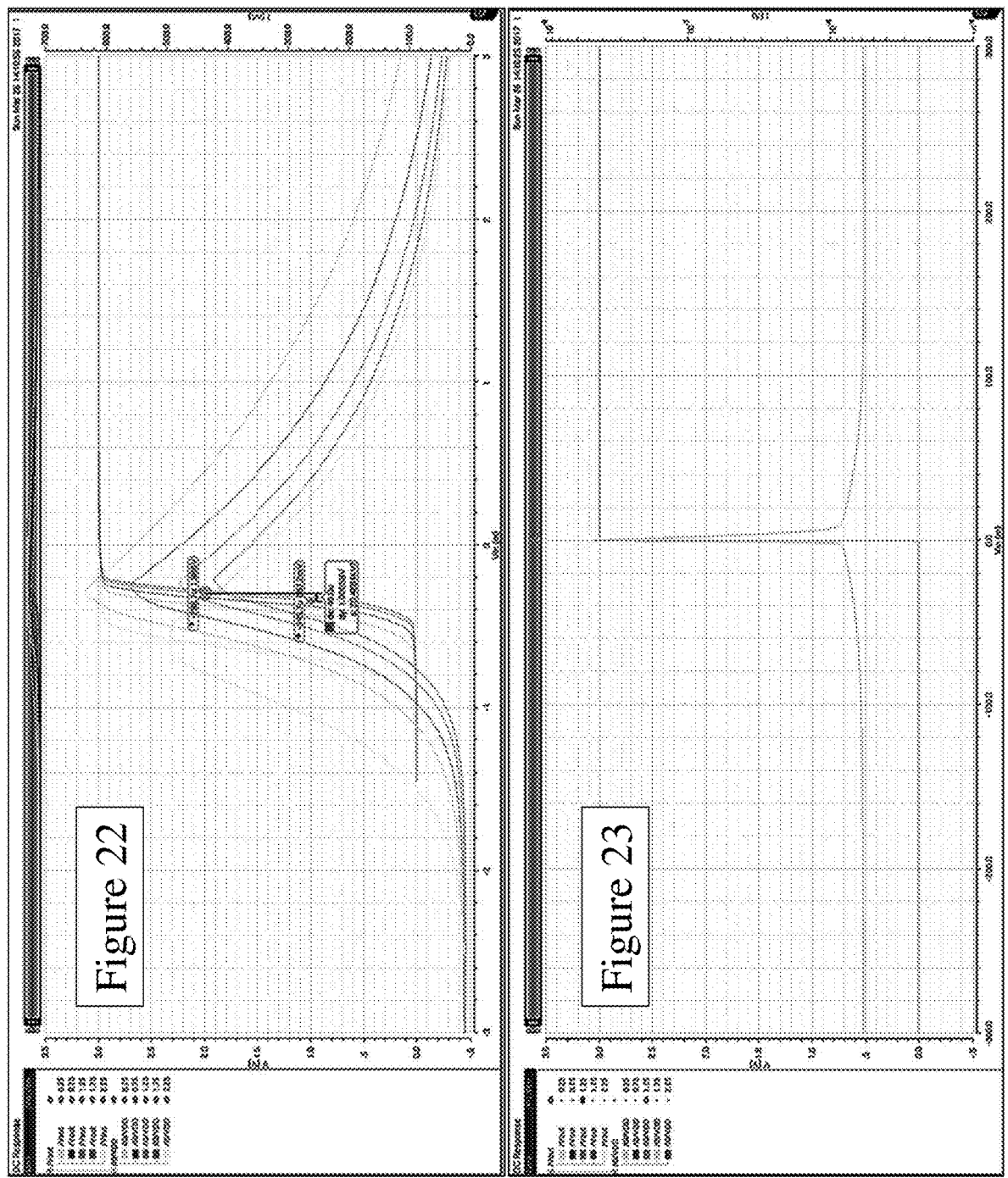

ULTRA WIDEBAND (UWB) TRANSMITTER AND RECEIVER CIRCUITS

CROSS-REFERENCE TO RELATED APPLICATIONS

This application claims the benefit of priority as a 371 National Phase entry of PCT/CA2020/000030 filed Mar. 18, 2020; which itself claims the benefit of priority from U.S. Provisional Patent Application 62/819,847 filed Mar. 18, 2019; the entire contents of each being incorporated herein by reference.

FIELD OF THE INVENTION

This invention relates to ultra-wideband wireless communication systems and more particularly to ultra-wideband transmitters and ultra-wideband receivers for such ultra-wideband wireless communication systems.

BACKGROUND OF THE INVENTION

Ultra-Wideband (UWB) technology is a wireless technology for the transmission of large amounts of digital data as modulated coded impulses over a very wide frequency spectrum with very low power over a short distance. Such pulse based transmission being an alternative to transmitting using a sinusoidal wave which is then turned on or off, to represent the digital states, as employed within today's wireless communication standards and systems such as IEEE 802.11 (Wi-Fi), IEEE 802.15 wireless personal area networks (PANs), IEEE 802.16 (WiMAX), Universal Mobile Telecommunications System (UMTS), Global System for Mobile Communications (GSM), General Packet Radio Service (GPRS), and those accessing the Industrial, Scientific and Medical (ISM) bands, and International Mobile Telecommunications-2000 (IMT-2000).

UWB systems are well-suited to short-distance applications in a variety of environments, such as depicted in FIG. 1 including peripheral and device interconnections, as exemplified by first residential environment 110, sensor networks, as exemplified by second residential environment 120, control and communications, as exemplified by industrial environment 130, medical systems, as exemplified by medical imaging 150, and personal area networks (PAN), as exemplified by PAN 140. Due to low emission levels permitted by regulatory agencies such UWB systems tend to be short-range indoor applications but it would be evident that a variety of other applications may be considered where such regulatory restrictions are relaxed and/or not present addressing military and civilian requirements for communications between individuals, electronic devices, control centers, and electronic systems for example.

Accordingly, it would be beneficial for UWB transmitters, UWB receivers and UWB transceivers to know precisely when to wake-up in deep sleep modes even though these devices exploit low frequency clock sources for ultra-low power consumption.

It would be beneficial for electronic circuits forming wireless radios to support low power operation by reducing current consumption where possible to exploit transistors or so-called compounded MOSFET structures whose effective gain and output resistance exceeds any single transistor irrespective of length.

It would be beneficial for electronic circuits forming wireless radios and other devices to support low power operation by employing a biasless low power differential (exponential) transconductance stage within operational transconductance amplifiers in order to provide very high gain low power amplification stages.

It would be beneficial for electronic circuits forming wireless radios to support low power operation by employing voltage reference sources that consume very low current, a few nA.

It would be beneficial for electronic circuits forming wireless radios to support low power operation by employing ultra-low power low dropout regulators.

Other aspects and features of the present invention will become apparent to those ordinarily skilled in the art upon review of the following description of specific embodiments of the invention in conjunction with the accompanying figures.

SUMMARY OF THE INVENTION

It is an object of the present invention to mitigate limitations within the prior art relating to ultra-wideband wireless communication systems and more particularly ultra-wideband transmitters and ultra-wideband receivers for such ultra-wideband wireless communication systems.

In accordance with an embodiment of the invention there is provided a method comprising: providing an electronic circuit comprising at least a DC-DC converter;
    establishing a sleep signal relating to powering down an electronic circuit into a sleep mode; turning off the DC-DC converter in dependence upon the establishment of the sleep signal;
    establishing a PLL clock counter to count the number of PLL clock cycles between the moment the sleep signal is raised and the moment the DC-DC converter is turned off;
    retaining the value of this PLL clock counter during the sleep mode;
    subtracting a time value established in dependence upon this retained PLL clock counter value from a predetermined delay relating to when to wake the electronic circuit out of the sleep mode.

In accordance with an embodiment of the invention there is provided a circuit comprising:
    a port for receiving a first signal to be coupled to the circuit;
    a PMOS gate and an NMOS gate electrically connected to the port in parallel and each connected to each other;
    a first portion of the circuit electrically connected to the PMOS gate; and
    a second portion of the circuit electrically connected to the NMOS gate; wherein
    the port behaves in the same manner as it would absent the PMOS gate and the NMOS gate; and
    the first portion and the second portion of the circuit now present twice the voltage threshold to the port.

In accordance with an embodiment of the invention there is provided a method comprising:
    providing a port for receiving a first signal to be coupled to the circuit;
    providing a PMOS gate and an NMOS gate electrically connected to the port in parallel and each connected to each other;
    providing a first portion of the circuit electrically connected to the PMOS gate; and
    providing a second portion of the circuit electrically connected to the NMOS gate; wherein
    for a slow rise transition within the first signal the actual input voltage has risen by the threshold voltage of the NMOS gate before a first node between the NMOS gate and the second portion of the circuit starts to rise in voltage and then become conductive;

as a gate connection of the NMOS gate is connected to a drain connection of the PMOS gate the voltage of the first node lags behind the voltage of a second node between the PMOS gate and the first portion of the circuit; and the roles between the NMOS gate and PMOS gate are a falling transition within the first signal.

In accordance with an embodiment of the invention there is provided a method comprising:

providing a first MOSFET comprising a first drain, a first gate, a first source and a first substrate connection;

providing a second n-channel MOSFET comprising a second drain, a second gate, a second source and a second substrate connection;

providing a first port electrically connected to the first gate, the second gate, and the first substrate connection;

providing a second port electrically connected to the first drain; and providing a third port electrically connected to the second source and the second substrate connection; wherein the first MOSFET and second MOSFET are the same and one of an n-channel MOSFET and a p-channel MOSFET.

In accordance with an embodiment of the invention there is provided an operational transconductance amplifier comprising:

at least a differential pair of compounded MOSFETs, each compounded MOSFET comprising:

a first MOSFET comprising a first drain, a first gate, a first source and a first substrate connection;

a second MOSFET comprising a second drain, a second gate, a second source and a second substrate connection;

a first port electrically connected to the first gate, the second gate, and the first substrate connection;

a second port electrically connected to the first drain;

a third port electrically connected to the second source and the second substrate connection;

and an electrical connection between the first source and the second drain; wherein the first MOSFET and the second MOSFET are the same type and at least one of an n-channel MOSFET and a PMOS MOSFET.

In accordance with an embodiment of the invention there is provided a current mirror comprising first to fourth compounded MOSFETs, each compounded MOSFET comprising a first MOSFET comprising a first drain, a first gate, a first source and a first substrate connection;

a second MOSFET comprising a second drain, a second gate, a second source and a second substrate connection; and a third MOSFET disposed between the first MOSFET and the second MOSFET comprising a third drain, a third gate, a third source and a third substrate connection; wherein the first port is electrically connected to the first gate, the second gate, the third gate and the first substrate connection;

the second port is electrically connected to the first drain;

the third port is electrically connected to the second source and the second substrate connection;

the third drain is connected to the first source;

the third source is connected to the second drain; and the third substrate connection is tied to the third drain such that the bias voltage of the third n-channel MOSFET is between the bias voltages of the first n-channel MOSFET and second n-channel MOSFET; wherein the first MOSFET, the second MOSFET and the third MOSFET are each a n-channel MOSFETs or a p-channel MOSFET.

In accordance with an embodiment of the invention there is provided a circuit comprising:

a biasless differential (exponential) transconductance stage comprising:

a pair of differential signal input ports;

first and second NMOS gates each coupled to one of the differential signal input ports;

first and second PMOS gates each coupled to one of the differential signal input ports; wherein either:

the sources of each of the first and second NMOS transistor and sources of the first and second PMOS gates are all connected together;

or the sources of the first and second NMOS transistor are connected together at first node of the circuit and the sources of the first and second PMOS gates are connected together at a second node of the circuit.

In accordance with an embodiment of the invention there is provided an operational amplifier comprising a biasless differential (exponential) transconductance stage comprising: a pair of differential signal input ports;

first and second NMOS gates each coupled to one of the differential signal input ports;

first and second PMOS gates each coupled to one of the differential signal input ports; wherein either:

the sources of each of the first and second NMOS transistor and sources of the first and second PMOS gates are all connected together;

or the sources of the first and second NMOS transistor are connected together at first node of the circuit and the sources of the first and second PMOS gates are connected together at a second node of the circuit.

In accordance with an embodiment of the invention there is provided a voltage source forming part of an electronic circuit comprising:

a current source; and a plurality of transistors disposed along a ladder of N electrical nodes; wherein node 0 is ground;

a gate of an $i^{th}$ transistor of the plurality of transistors is connected to node i−1;

a source of the $i^{th}$ transistor of the plurality of transistors is connected to node i;

a drain of the $i^{th}$ transistor of the plurality of transistors is connected to node i+1; and the current sources are disposed within the gap left within the current path between node 0 and node 1.

In accordance with an embodiment of the invention there is provided a method of providing a voltage source forming part of an electronic circuit comprising:

providing a plurality of N native transistors in a serial array; wherein a source of a native transistor i of the plurality of N native transistors is coupled to a drain of a native transistor i−1 of the plurality of N active transistors where i=2, ..., N;

a source of the first native transistor of the plurality of N native transistors is coupled to ground;

a substrate of a native transistor j of the plurality of N native transistors is coupled to ground where j=1, ..., N; and a gate of a native transistor k of the plurality of N native transistors is coupled to a node between the source of a transistor k−1 of the plurality of N active transistors and a drain of a native transistor k−2 of the plurality of N active transistors where k=3, ..., N and k is an integer.

In accordance with an embodiment of the invention there is provided a method of providing a low dropout regulator for an electronic circuit comprising:

providing a high impedance reference voltage supply;

providing a pair of first transistors to isolate an output of a reference voltage circuit from any digital noise fed through from a source of a second transistor to a gate of the second transistor; wherein an upper first transistor and a lower first transistor disposed in series between an upper power rail and ground;

a drain of the upper first transistor is connected to the upper power rail and a source of the lower first transistor is connected to ground;

a gate of the second transistor, a source of the upper first transistor and a drain of the lower first transistor are all coupled to a common node; and the high impedance reference voltage supply is coupled to a gate of the lower first transistor and a gate of the upper first transistor.

In accordance with an embodiment of the invention there is provided an electronic circuit comprising a plurality of electronic circuit elements; and a dynamically biased pre-amplifier with latched comparator comprising:

an NMOS input differential pair disposed between a pair of differential input ports;

a PMOS input differential pair disposed between the pair of differential input ports; and a dynamic bias circuit coupled to the sources of the PMOS input differential pair.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein:

FIG. 1 depicts applications of UWB transmitters, receivers, and systems according to embodiments of the invention;

FIG. 17 displays the output from an OTA according to an embodiment of the invention with DC voltage offset between the inputs;

FIG. 18 depicts simulation results for an operational transconductance amplifier according to an embodiment of the invention exhibiting open-loop gain of 76 dB and gain bandwidth product of 25 MHz;

FIG. 19 depicts the power spectral density of the noise simulation of an operational transconductance amplifier according to an embodiment of the invention;

FIG. 20 depicts the rise time/fall time simulation results for an operational transconductance amplifier according to an embodiment of the invention;

FIG. 22 depicts the DC transfer function with open loop DC gain ~85 dB with an input range between V_SS +0.2V and V_DD −0.7V for the operational amplifier employing a biasless low power differential (exponential) transconductance stage according to an embodiment of the invention as depicted in FIG. 21;

FIG. 23 depicts continuous current results for the operational amplifier employing a biasless low power differential (exponential) transconductance stage according to an embodiment of the invention as depicted in FIG. 21;

DETAILED DESCRIPTION

Figure 2:
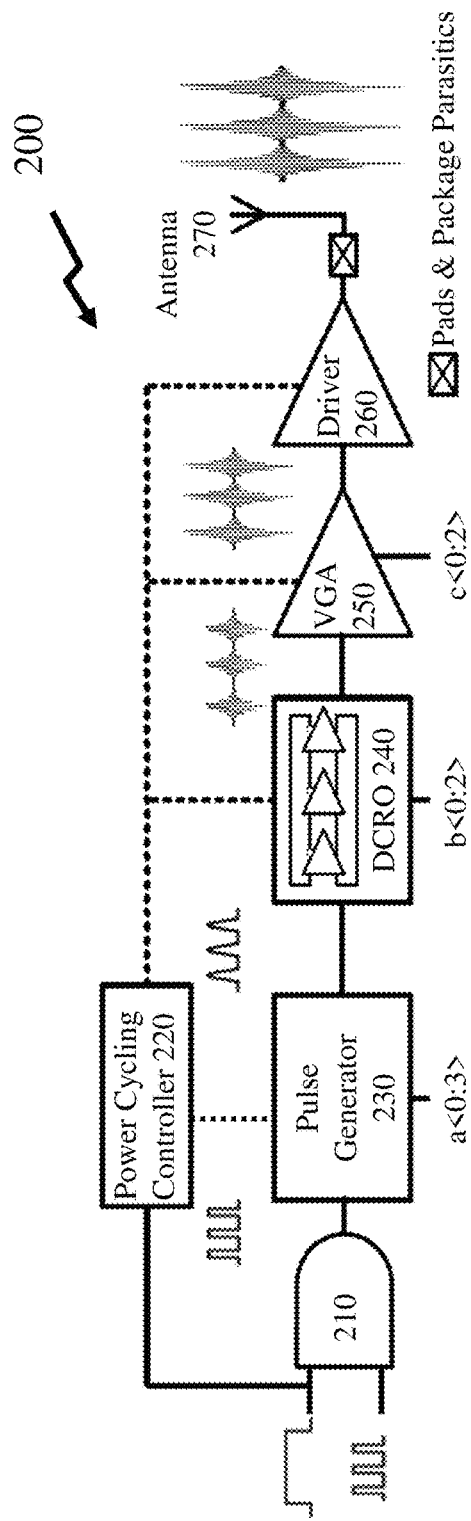
FIG. 2 depicts a block diagram of a UWB transmitter according to an embodiment of the invention.

The present invention is directed to ultra-wideband wireless communication systems and more particularly ultra-wideband transmitters and ultra-wideband receivers for such ultra-wideband wireless communication systems.

The ensuing description provides exemplary embodiment(s) only, and is not intended to limit the scope, applicability or configuration of the disclosure. Rather, the ensuing description of the exemplary embodiment(s) will provide those skilled in the art with an enabling description for implementing an exemplary embodiment. It being understood that various changes may be made in the function and arrangement of elements without departing from the spirit and scope as set forth in the appended claims.

0. Impulse Radio Ultra Wideband System

As discussed supra UWB offers many potential advantages such as high data rate, low-cost implementation, and low transmit power, ranging, multipath immunity, and low interference. The Federal Communications Commission (FCC) regulations for UWB reserved the unlicensed frequency band between 3.1 GHz and 10.6 GHz for indoor UWB wireless communication system wherein the low regulated transmitted power allows such UWB systems to coexist with other licensed and unlicensed narrowband systems. Therefore, the limited resources of spectrum can be used more efficiently. On the other hand, with its ultra-wide bandwidth, an UWB system has a capacity much higher than the current narrowband systems for short range applications. Two possible techniques for implementing UWB communications are Impulse Radio (IR) UWB and multi-carrier or multi-band (MB) UWB. IR-UWB exploits the transmission of ultra-short (of the order of nanosecond) pulses, although in some instances in order to increase the processing gain more than one pulse represents a symbol. In contrast MB-UWB systems use orthogonal frequency division multiplexing (OFDM) techniques to transmit the information on each of the sub-bands. Whilst OFDM has several good properties, including high spectral efficiency, robustness to RF and multi-path interferences. However, it has several drawbacks such as up and down conversion, requiring mixers and their associated high power consumption, and is very sensitive to inaccuracies in frequency, clock, and phase. Similarly, non-linear amplification destroys the orthogonality of OFDM. Accordingly, MB-UWB is not suitable for low-power and low cost applications.

In contrast IR-UWB offers several advantages, including unlicensed usage of several gigahertz of spectrum, offers great flexibility of spectrum usage, and adaptive transceiver designs can be used for optimizing system performance as a function of the data rate, operation range, available power, demanded quality of service, and user preference. Further, multi-Gb/s data-rate transmission over very short range is possible and due to the ultra-short pulses within IR-UWB it is very robust against multipath interference, and more multipath components can be resolved at the receiver in some implementations, resulting in higher performance. Further, the ultra-short pulses support sub-centimeter ranging whilst the lack of up and down conversion allows for reduced implementation costs and lower power transceiver implementations. Beneficially, ultra-short pulses and low power transmissions make IR-UWB communications hard to eavesdrop upon.

An IR-UWB transmitter as described below in respect of embodiments of the invention in with reference to FIGS. 2 and 3 respectively exploits an on-demand oscillator following a pulse generator in order to up-convert the pulses from the pulse generated whilst avoiding the requirement of a separate mixer. Implementable in standard CMOS logic both the pulse generator and the on-demand oscillator are digitally tunable in order to provide control over the pulse bandwidth and center frequency. Further, by exploiting a digitally controlled ring oscillator for the on-demand oscillator the IR-UWB transmitter is designed to allow very quick frequency adjustments on the order of the pulse repetition rate (PRR). Beneficially this technique provides the same advantages as MB-OFDM in respect of spectrum configurability, achieved by sequentially changing the transmitted spectrum using a frequency hopping scheme, whilst maintaining the benefits of IR-UWB. Further, by providing advanced duty cycling with fast power up time combined with On-Off Shift Keying (OOK) modulation the IR-UWB according to embodiments of the invention allows significant reductions in power consumption by exploiting the low duty cycle of a UWB symbol and the fact that only half the symbols require sending energy.

In addition to defining the operating frequency range for UWB systems the different regulatory bodies all specify and enforce a specific power spectral density (PSD) mask for UWB communications. A PSD mask as may be employed in respect of embodiments of the invention is the FCC mask for which mask data are summarized in Table 1 below for the 3100 MHz-10600 MHz (3.1 GHz-10.6 GHz) range.

TABLE 1

FCC Masks for Indoor - Outdoor for Different Frequency Bands

| Frequency Range | Indoor EIRP Limit (dBm/MHz) | Outdoor EIRP Limit (dBm/MHz) |
|---|---|---|
| <960 | −49.2 | −49.2 |
| 960-1610 MHz | −75.3 | −75.3 |
| 1610-1990 MHz | −53.3 | −63.3 |
| 1990-3100 MHz | −51.3 | −61.3 |
| 3100-10600 MHz | −41.3 | −41.3 |
| >10600 MHz | −51.3 | −61.3 |

Accordingly, it would be evident that the upper limit of −41.3 dB/MHz across the 3.1 GHz-10.6 GHz frequency range is the same limit imposed on unintentional radiation for a given frequency in order not to interfere with other radios. Basically, for a given frequency, the UWB radio operates under the allowed noise level which creates the relationship presented in Equation (1) between $E_p$, the transmitted energy per pulse, the maximum spectral power S, the bandwidth B, the bit rate $R_b$ and the number of pulses per bits $N_{ppb}$.

$$E_p \cdot N_{ppb} \cdot R_b \leq S \cdot B \quad (1)$$

The IEEE has published a few standards for a physical layer (PHY) for UWB radio in Personal Area Networks (IEEE 802.15.4a-2007), Body Area Networks (IEEE 802.15.4a-2007) and Radio-Frequency Identification (IEEE 802.15.4f-2012). These standards use mostly relatively large pulses resulting in relatively narrow bandwidth which is up-converted to a specific center frequency in order to fill predetermined channels. The data is encoded using pulse-position-modulation (PPM) and bi-phasic shift keying (BPSK) is used to encode redundancy data. Every bit consists of one or more pulses scrambled in phase depending on the target data rate. These standards allow considerable flexibility on channel availability and data rates. The standard also defines the preamble, headers for the data packet and ranging protocol.

These IEEE standards are designed with multiple users in mind and use different channels to transmit the data, thereby putting a heavy constraint on pulse bandwidth and limiting the transmitted energy. Prior art on non-standard transmitter attempts to make better use of the available spectrum by using narrow pulses, which therefore have a larger bandwidth thereby increasing the maximum transmitted energy according to Equation (1). Accordingly, these transmitters are non-standard and were also designed for different data rates, frequencies, pulse width, etc. Additionally, they also used various encoding schemes, most notably PPM, OOK or BPSK.

Within the work described below the inventors have established improvements with respect to UWB systems, UWB transmitters and energy based UWB receivers which are capable of generating and adapting to a variety of IR-UWB pulses and bit encoding schemes thereby supporting communications from both IR-UWB transmitters compliant to IEEE standards as well as those that are non-standard. These improvements are made with respect to UWB transmitters, UWB receivers, UWB transceivers and UWB systems such as those described and depicted by the inventors within WO/2019/000075 "Energy Efficient Ultra-Wideband Impulse Radio Systems and Methods" (PCT/CA2018/000,135 filed Jun. 29, 2018); WO 2016/191851 "Systems and Methods for Spectrally Efficient and Energy Efficient Ultra-Wideband Impulse Radios with Scalable Data Rates" (PCT/CA2016/000,161 filed May 31, 2016); and WO/2015/103,692 "Systems and Methods Relating to Ultra Wideband Broadcasting comprising Dynamic Frequency and Bandwidth Hopping" (PCT/CA2015/000,007, filed Jan. 7, 2015)."

1. IR-UWB Transmitter Circuit

Referring to FIG. 2 there is depicted schematically an exemplary architecture for an IR-UWB transmitter 200 according to embodiments of the invention which is composed of five main blocks plus the antenna. First a programmable impulse is produced by a pulse generator 230 at clocked intervals when the data signal from AND gate 210 is high based upon control signals presented to the AND gate 210. The pulses from the pulse generator 230 are then up-converted with a programmable multi-loop digitally controlled ring oscillator (DCRO) 240. The output from the DCRO 240 is then coupled to a variable gain amplifier (VGA) 250 in order to compensate for any frequency dependency of the pulse amplitude. Finally, a driver 260 feeds the antenna 270, overcoming typical package parasitics, such as arising from packaging the transceiver within a quad-flat no-leads (QFN) package. In order to further reduce the power consumption of the IR-UWB transmitter (IR-UWB-Tx) 200 according to embodiments of the invention a power cycling controller 220 dynamically switches on or off these functional blocks when the data signal is low.

Figure 3A:
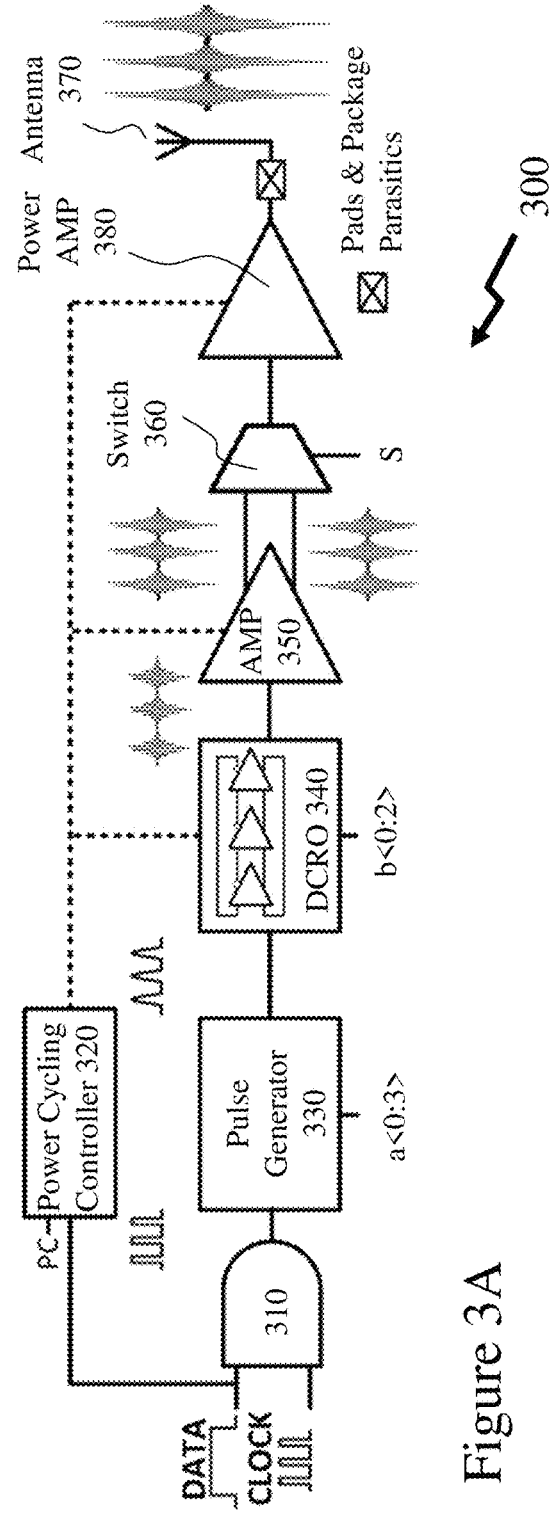
FIG. 3A depicts a block diagram of a UWB transmitter according to an embodiment of the invention supporting biphasic phase scrambling.

Now referring to FIG. 3A there is depicted schematically a block diagram 300 of an exemplary IR-UWB transmitter according to embodiments of the invention supporting biphasic phase scrambling. In comparison to the IR-UWB transmitter 200 in FIG. 2 for an IR-UWB according to embodiments of the invention without biphasic phase shifting rather than being composed of five main blocks plus the antenna the Biphasic Phase Shifting IR-UWB (BPS-IR-UWB) transmitter comprises 6 main blocks. First a programmable impulse is produced by a pulse generator 330 at clocked intervals when the data signal from AND gate 310 is high based upon control signals presented to the AND gate 310. The pulses from the pulse generator 330 are then up-converted with a programmable multi-loop digitally controlled ring oscillator (DCRO) 340. The output from the DCRO 340 is then coupled to a dual-output amplifier (VGA) 350 both in order to compensate for any frequency dependency of the pulse amplitude but also to generate dual phase shifted output signals that are coupled to a switch 360 which selects one of the two signals to couple to the output power amplifier (driver) 380 under the action of the switch control signal "S" applied to the switch 360. Note that a similar phase selection scheme could be implemented by affecting the startup conditions o DCRO 340 in order to provide the two phases. This would preclude the need for switch 360 at the cost of an added control startup condition control signal on DCRO 340.

The output power amplifier 380 feeds the antenna 370, overcoming typical package parasitics, such as arising from packaging the transceiver within a quad-flat no-leads (QFN) package. In order to reduce the power consumption of the BPS-IR-UWB transmitter represented by block diagram 300 according to an embodiment of the invention a power cycling controller 320 dynamically switches on or off these functional blocks when the data signal "PC" is low. Accordingly, a BPS-IR-UWB transmitter according to embodiments of the invention transmits pulses with or without phase shift based upon the control signal "S" applied to switch 360. If this control signal is now fed from a random data generator or a pseudo-random data generator then the resulting pulses coupled to the antenna of the BPS-IR-UWB transmitter will be pseudo-randomly or randomly phase shifted.

Figure 3B:
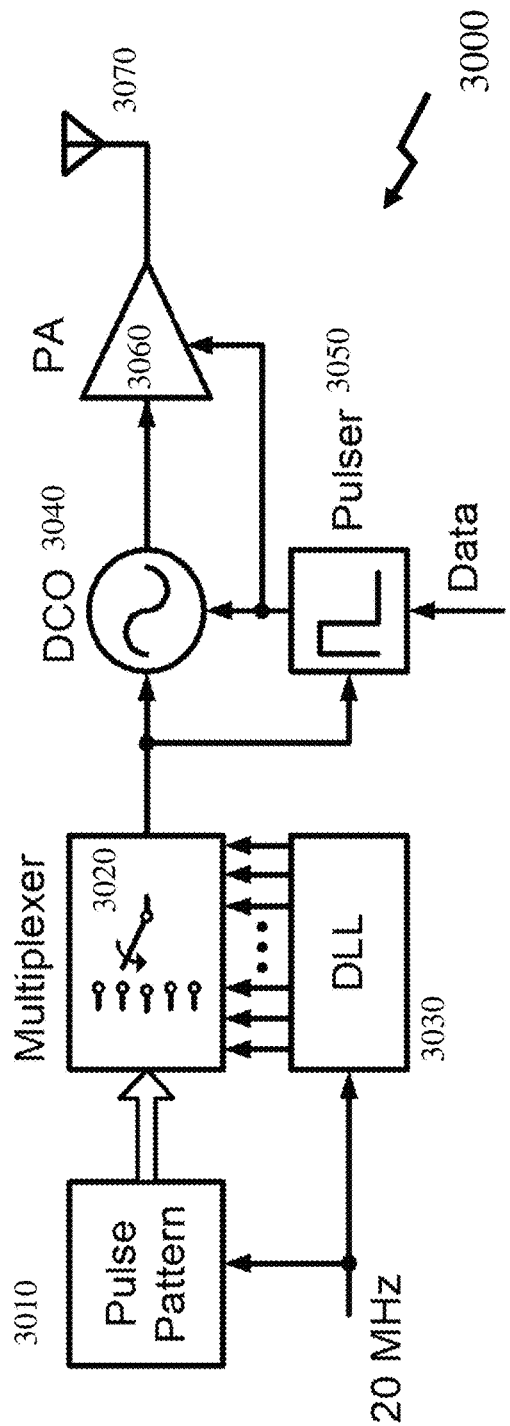
FIG. 3B depicts a block diagram of a UWB transmitter according to an embodiment of the invention employing dynamically configurable and programmable pulse sequences.

Now referring to FIG. 3B there is depicted schematically a block diagram 3000 of an exemplary IR-UWB transmitter according to embodiments of the invention. As depicted a Pulse Pattern block 3010 holds a configuration for the pulses used to represent the current symbol. From the symbol-rate clock (i.e. 20 MHz), multiple phases are generated by a Delay Locked Loop (DLL) 3030. The rising edge of each clock phase represents the start of one pulse in the symbol pulse bundle. A multiplexer 3020 is triggered by the edges of the clock phases and selects the configuration of the current pulse out of the Pulse Pattern block 3010. A pulse generator (Pulser) 3050 generates pulses with a pulse width set by the multiplexer 3020 and enables the Digitally Controlled Oscillator (DCO) 3040 and Power Amplifier (PA) 3060. When enabled, the DCO 3040 generates a Gaussian shaped pulse with frequency set by the multiplexer 3020, which is then amplified by the PA 3060 and radiated by the antenna 3070.

Accordingly, the Pulse Pattern block 3010 establishes the pulses for a symbol or sequence of symbols. In this manner updating the Pulse Pattern block 3010 adjusts the pulse sequence employed for each symbol and accordingly the Pulse Pattern block 3010 may be dynamically updated based upon one or more factors including, but not limited to, network environment data, predetermined sequence, date, time, geographic location, signal-to-noise ratio (SNR) of received signals, and regulatory mask.

Figure 3C:
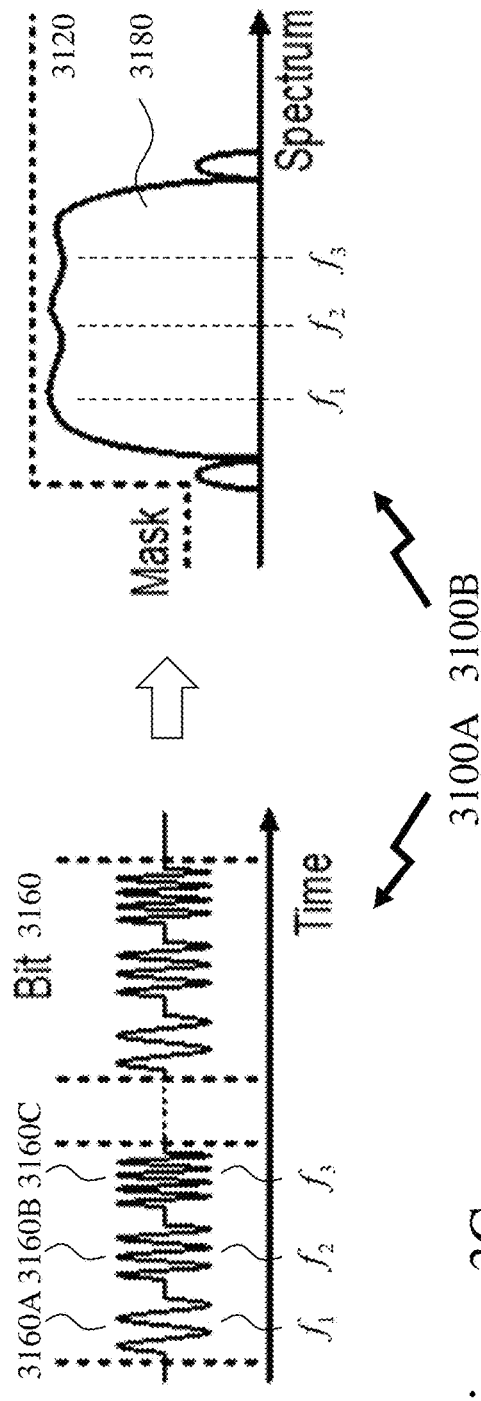
FIG. 3C depicts schematically a multi-pulse symbol UWB protocol according to an embodiment of the invention.

Referring to FIG. 3C there is depicted schematically a multi-pulse symbol UWB protocol according to an embodiment of the invention. Referring to first image 3100A there is depicted a bit 3160 comprising a series of sub-pulses 3160A to 3160C which are each at frequencies $f_1$; $f_2$; $f_3$. Accordingly, the multi-pulse spectrum 3180 of a symbol (bit 3160) is depicted in second image 3100B as obtained conceptually (phase scrambling is omitted for clarity) by summing the individual pulse spectra of the sub-pulses 3160A to 3160C, which increases the bandwidth whilst increasing the total symbol duration, in contrast with single-pulse prior art methods, whilst maintaining the maximum power below the UWB mask 3120. This allows the symbol energy to be maximized while relaxing the timing requirements and level of synchronization required at the receiver. An arbitrary number of pulses with different sets of parameters may be included within a bundle to tailor the pulse spectrum to a given requirement.

2. IR-UWB Receiver

Figure 4:
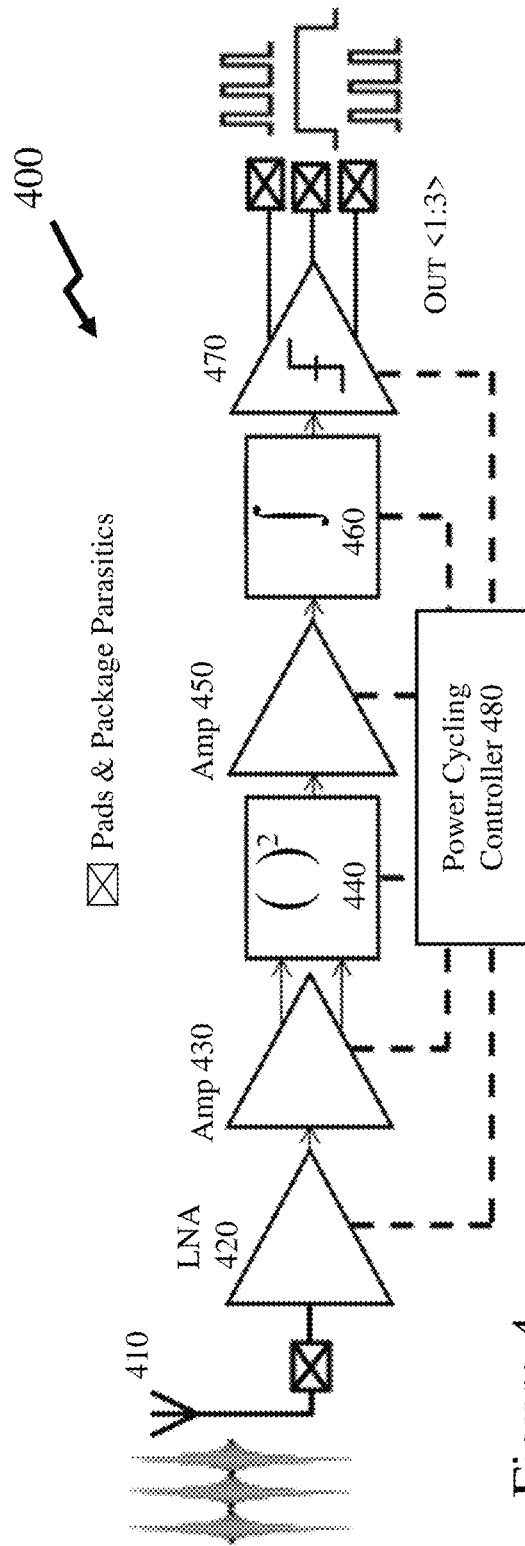
FIG. 4 depicts a block diagram of a UWB receiver according to an embodiment of the invention.

Referring to FIG. 4 there is depicted schematically the architecture of an IR-UWB receiver 400 according to embodiments of the invention. Accordingly, the signal from an IR-UWB transmitter is received via an antenna 410 and coupled to a low noise amplifier (LNA) 420 followed by first amplifier 430 wherein the resulting signal is squared by squaring circuit 440 in order to evaluate the amount of energy in the signal. The output of the squaring circuit 440 is then amplified with second amplifier 450, integrated with integration circuit 460 and evaluated by a flash ADC 470 to generate the output signals. Also depicted is Power Cycling Controller 480 which, in a similar manner to the power cycling controller 220 of IR-UWB transmitter 200 in FIG. 2, dynamically powers up and down the LNA 420, first and second amplifiers 430 and 450 respectively, squaring circuit 440, and flash ADC 470 to further reduce power consumption in dependence of the circuit's requirements.

Figure 5:
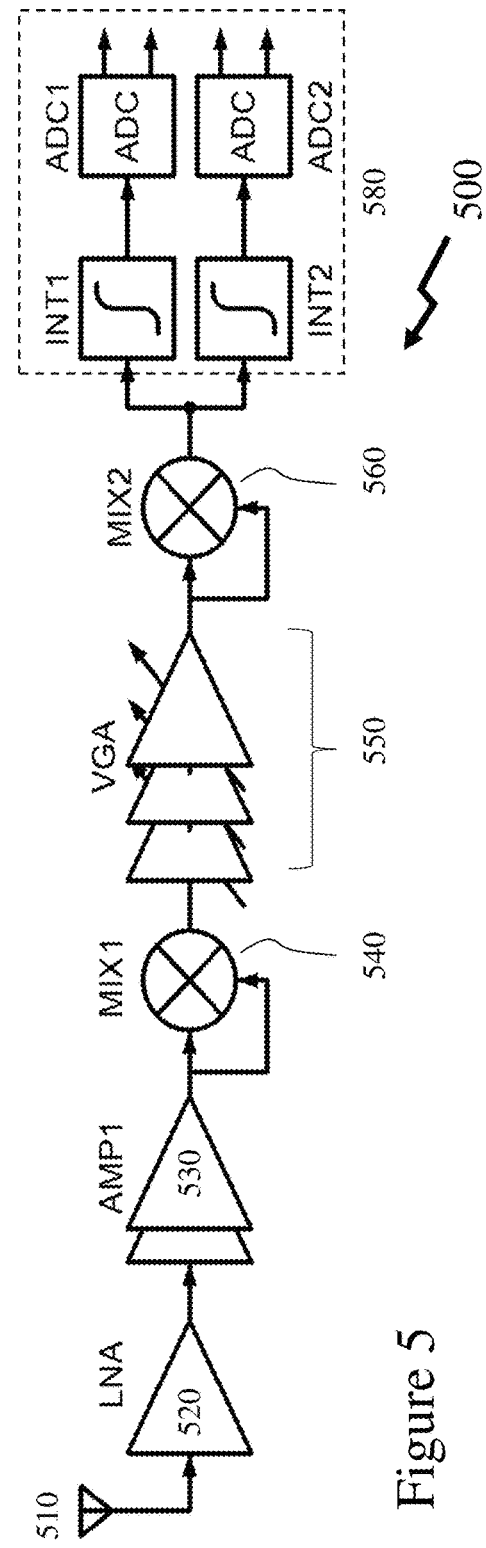
FIG. 5 depicts a receiver circuit schematic for a UWB receiver/transceiver according to an embodiment of the invention.

Referring to FIG. 5 there is depicted a schematic of a receiver 500 according to an embodiment of the invention. The RF signal from the antenna 510 is initially amplified by a Low Noise Amplifier (LNA) 520 before being passed to a two stage RF amplifier (AMP1) 530. A first squaring mixer (MIX1) 540 multiplies the signal with itself to convert to the Intermediate Frequency (IF). A three-stage Variable Gain Amplifier (VGA) 550 amplifies the signal further and implements a bandpass filter function. The VGA 550 output is then coupled to a second squaring mixer (MIX2) 560 which down-converts the signal to the baseband frequency. A parallel integrator (INT1 and INT2) sums the signal energy, which is digitized by the Analog-to-Digital Converters (ADC1 and ADC2) within a digital processor (not depicted for clarity).

3. IR-UWB Receiver

As described within WO/2019/000075 and WO 2016/191851 the inventors have established design parameters of millisecond range start-up time from sleep mode and microsecond range start-up time from idle mode by establishing a custom integrated DC/DC converter and duty cycled transceiver circuitry that enables fast circuit start-up/shut-down for optimal power consumption under low (1 kbps) and moderate data rates (10 Mbps).

Figure 6:
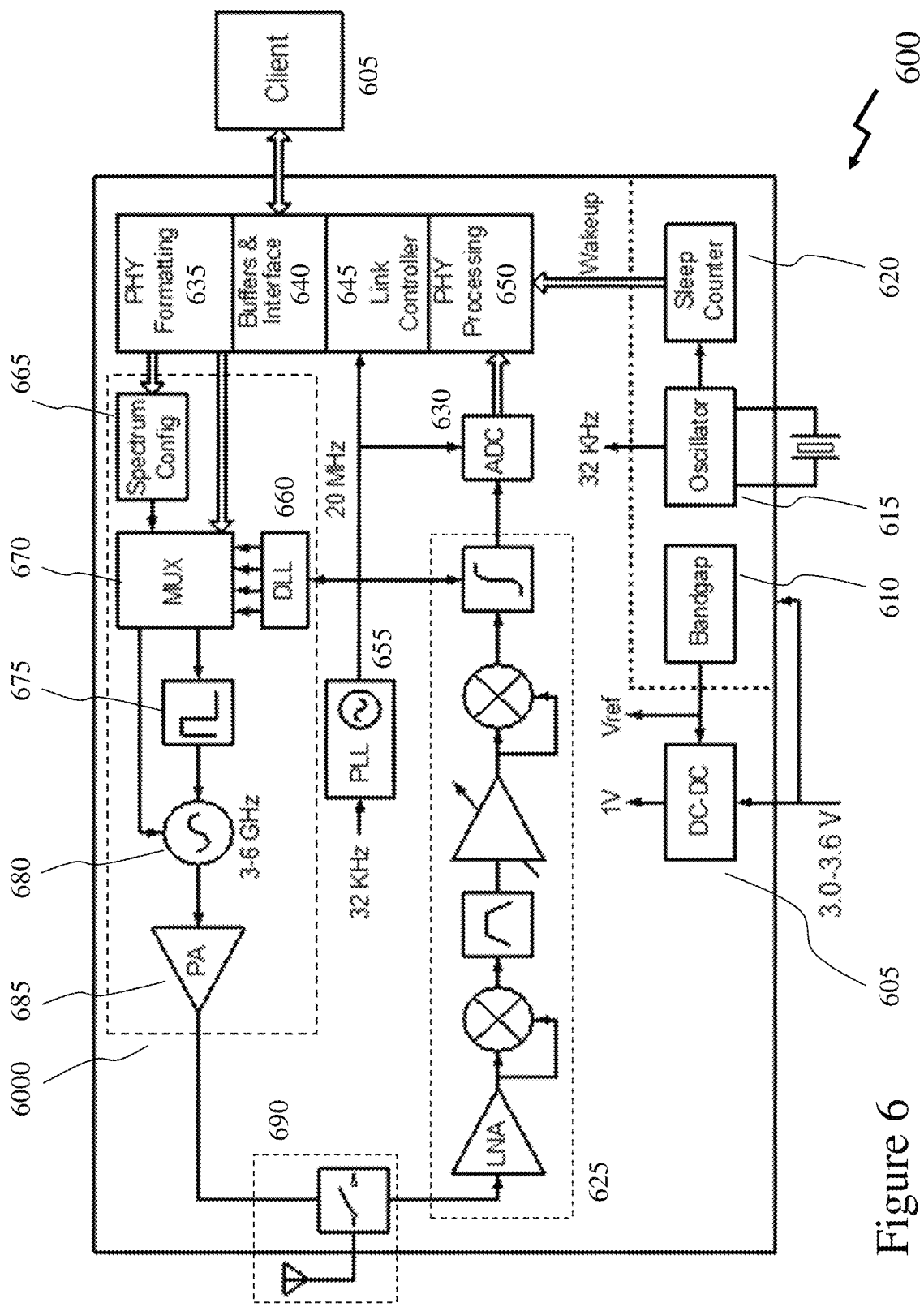
FIG. 6 depicts a circuit schematic for a UWB transceiver according to an embodiment of the invention.

In order to sustain good energy efficiency, the elements of a total UWB transceiver, such as depicted with transceiver 600 in FIG. 6 according to embodiments of the invention, has been designed for low static sleep current and fast startup/sleep times. Referring to FIG. 6, a battery (3.0 V≤$V_{BATT}$≤3.6 V) (not depicted for clarity) powers a low-frequency crystal oscillator 615, sleep counter 620 and bandgap reference 610, all of which are typically always operational although the bandgap reference 610 could be duty cycled within other embodiments of the invention without altering the scope of the claimed invention). Their power consumption limits the minimum power consumption of the system to sub-microwatt level. An integrated buck DC-DC converter 605 is powered by the battery when the system is not in sleep mode, and this provides the supply voltage to the rest of the system with high conversion efficiency. The startup time of the DC-DC converter 605 is on the order of several symbol periods in order to minimize wasted energy. Between sleep periods, the PLL 655 is active to provide the base clock for the system. The receiver 625 and DLL 660 have dedicated power down controls and are only activated during frame transmission/reception. Further, the transmitter is also power cycled through its all-digital architecture which is not depicted as having a separate control. The power consumption of the digital synthesized blocks is low due to the low base clock (e.g. 20 MHz).

In principle, a power-cycled transceiver achieves linear scaling of power consumption with data rate, thus achieving constant energy efficiency. With a fixed frame size, multiple data rates are obtained by adjusting the length of the sleep period, with the maximum attainable data rate determined by the symbol rate in the frame itself. In order to preserve energy efficiency, the power consumption during sleep must be lower than the average power consumption. For high data rates, powering down the PLL is not required when its consumption does not significantly degrade the overall efficiency. For low data rates, the whole system except the bandgap reference, crystal oscillator, and sleep counter can be shut down during sleep mode. In this case, the millisecond range startup time of the PLL can be insignificant compared to the sleep period, and overall efficiency is also not significantly degraded.

As depicted the UWB transceiver 600 also comprises a receive/transmit switch 690 coupled to the antenna to selectively couple the transmitter 6000 or receiver 625 to the antenna during transmission and receipt respectively. The UWB transceiver 600 also comprises a spectrum configuration circuit 665 (equivalent to Pulse Pattern 3010 in transmitter 3000 in FIG. 3B), PHY Processing circuit 650, Link Controller 645, Buffer and Interface circuit 640, and PHY Formatting circuit 635. The UWB transceiver 600 communicates via Link Controller 645 to the Client 605. As such, Link Controller 645 may communicate using a wired protocol to Client 605, for example.

4. Crystal Clock Drift Compensation

Within UWB transmitters, UWB receivers and UWB transceivers described by the inventors within WO/2019/000075 and WO 2016/191851 ultra-low power consumption is achieved through both fundamental design considerations of the electronic circuit itself, exploitation of a low frequency clock, and the implementation of aggressive sleep cycling of portions of the electronic circuit according to the state of the device and those portions of the electronic circuit required to perform particular functions in each state.

Within these devices a phase locked loop (PLL) generates a high speed clock which is operating significantly faster than the crystal oscillator providing the underlying base frequency of the electronic circuit. Accordingly, the electronic circuits exploit the PLL to up-convert a low power low frequency clock and generate the requisite sub-clocks rather than employing a high power high frequency clock and dividing that to generate the requisite sub-clocks.

However, when the electronic circuit enters a low power consumption mode wherein even the DC-DC converter, such as DC-DC Converter 605 in FIG. 6, is powered down in what the inventors refer to as "DCDC Sleep" then the PLL clock signal does not propagate through to the digital portions of the electronic circuits and accordingly cannot be employed to determine when to wake the electronic circuits up again and hence wake up the wireless radio comprising these electronic circuits. In this DCDC Sleep the only clock propagating is the 32 kHz crystal clock signal which if used alone would provide an error potentially in excess of 30 µs with respect to when to wake up the electronic circuits and wireless radio. Whilst other "deeper" sleep power modes of a wireless circuit according to embodiments of the invention may exist the solution described herein address the current case and these deeper sleep modes. The constraint being that within the sleep modes to which the invention relates there is no longer a PLL clock reaching the digital circuit(s) which contain the PLL clock counter.

Figure 7:
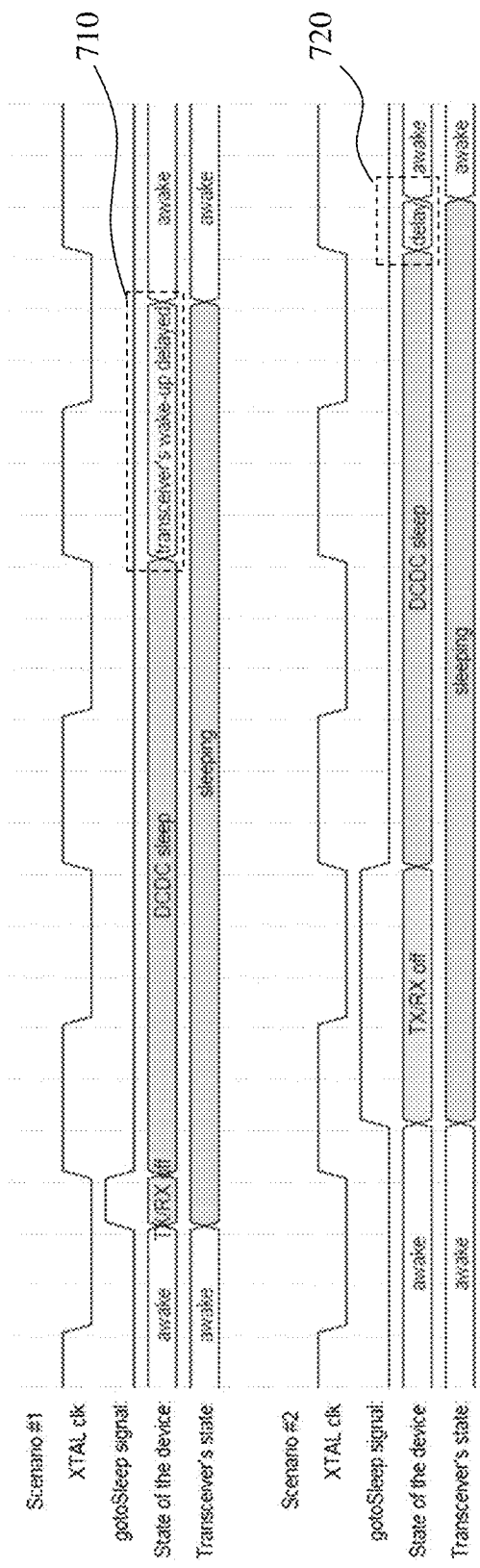
FIG. 7 depicts schematically the use of a counter retained during deep sleep levels which is subtracted from the additional delay in the exemplary timing scenarios for UWB wireless radios according to embodiments of the invention

Accordingly, in order to mitigate this problem a PLL clock counter is implemented which counts the number of PLL clock cycles between the moment the signal to go to sleep is raised and the moment the DC-DC converter is actually turned off. Due to the design of the electronic circuit this is always on a predetermined edge of the next crystal clock cycle, for example the rising edge as depicted in FIG. 7. The value of this counter is retained during deep sleep levels and is subtracted from the additional delay labeled Transceiver's Wake-Up Delayed 710 in FIG. 7 in Scenario #1 and Delay 720 in FIG. 7 in Scenario #2 after the DC-DC converter wake-up. Accordingly, the sleep duration of the electronic circuits and wireless radio are now independent of the point within the period of the crystal clock cycle when the sleep signal is raised, and the electronic circuits and wireless radio turns off. Whilst the embodiment of the invention has been described with respect to a 32 kHz clock as described within WO/2019/000075 and WO 2016/191851 it would be evident that other base clock frequencies may be employed and that the method described is also independent of the phase of the clock, e.g. crystal clock. The DC-DC converter is turned off upon a predetermined edge of the crystal clock cycle.

5. CMOS Crossover Current Reduction Stage

Figure 8:
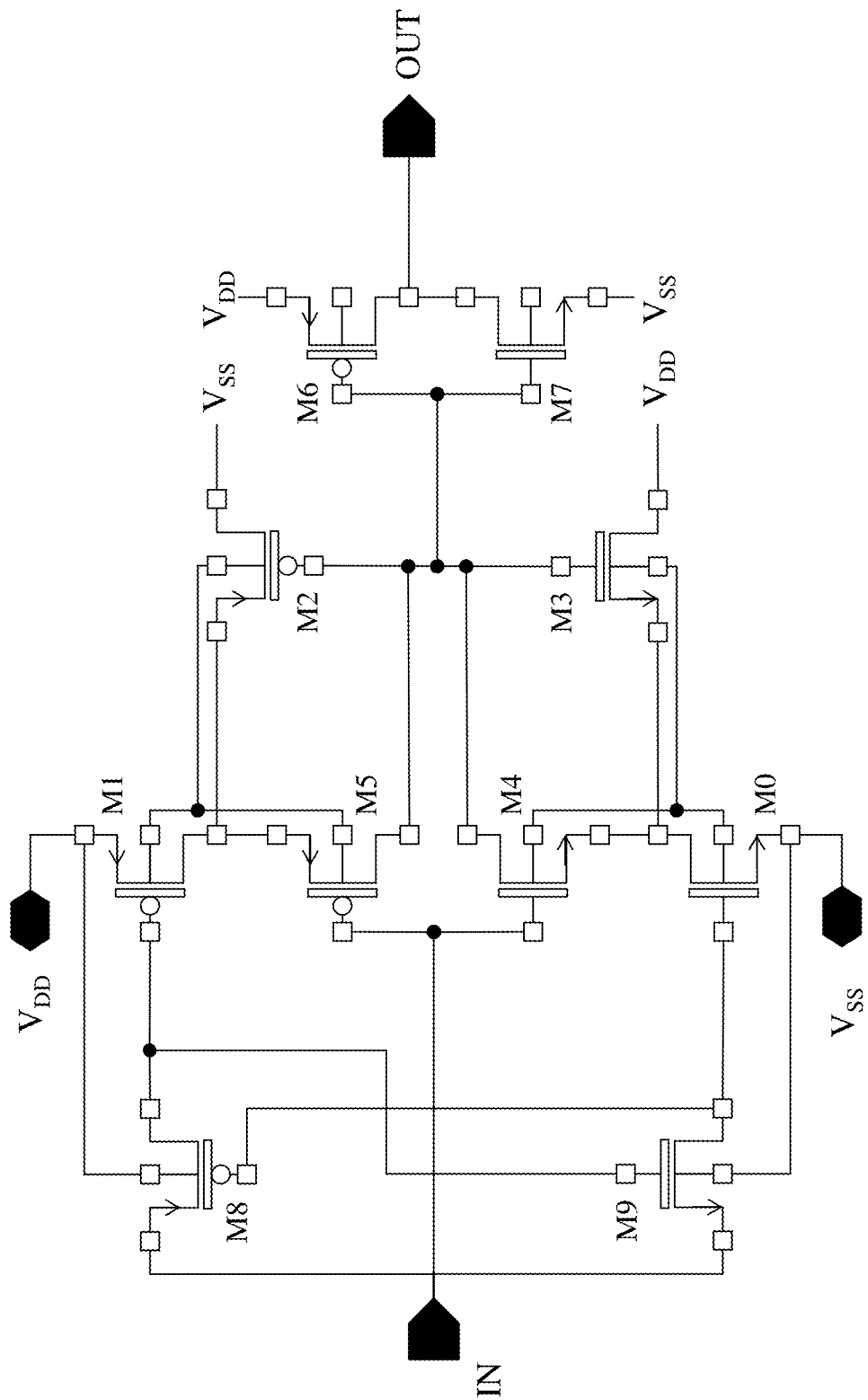
FIG. 8 depicts a CMOS crossover current reduction stage according to an embodiment of the invention connected to a traditional Schmitt trigger.

Within UWB transmitters, UWB receivers and UWB transceivers exploiting Complementary Metal-Oxide-Semiconductor (CMOS) technology it is beneficial for many applications to provide ultra-low power consumption as a requirement. Accordingly, minimizing current within the CMOS circuits is a requirement and any reductions beneficial to the overall electronic circuit. According to embodiments of the invention a dual transistor structure, identified as transistors M8 and M9 in FIG. 8, are inserted in the input to raise the required fraction of any voltage transition to turn on the transistors of the digital input to which it is connected to. The dual transistor structure acts to double the effective voltage threshold of the digital input which has the benefit of reducing the crossover current during long voltage transitions at the input. This circuit may also be beneficial for a Schmitt trigger and could replace a Schmitt trigger although it would be beneficial to place the circuit in front of a Schmitt trigger.

Accordingly, referring to FIG. 8 then the digital input behaves in the same manner but now as if the transistors it was previously connected to, namely M0 and M1, have twice the voltage threshold. Whilst the dual transistor structure does not actually reduce the leakage current beyond its nominal level when $V_{gs}=0$ it adjusts the energy efficiency during any voltage transition. Accordingly, the voltage difference between the electrical nodes pmos_gate and nmos_gate is about one time the voltage threshold of the transistors used in the dual transistor structure, namely M8 and M9, therefore reducing the $V_{gs}$ of transistors M0 and M1 by one voltage threshold as long as the result is above 0 volts. Whilst, within FIG. 8 the bulk contacts of M8 and M9 do not have to be connected to $V_{DD}$ or $V_{SS}$. These bulk contacts may alternatively be tied to the corresponding sources or drains of the transistors M8 and M9.

Hence, the result is that for every (slow) rise transition, the actual input voltage will have to rise by the threshold voltage of the NMOS M9 before the node nmos_gate starts to rise in voltage since the transistor M9 has to first become conductive. Then because its gate is connected to the drain of M8 through the node pmos_gate, the voltage of node nmos_gate "lags" behind the voltage of pmos_gate. This is because it has to wait for the pmos_gate node to further charge the gate of M9 to allow the node nmos_gate to keep rising in voltage during the transition. The roles are simply reversed between M8 and M9 for a falling transition and the underlying concept is identical.

Accordingly, the primary benefit of this design is that the crossover current, when the input voltage is in the middle of a transition and both M0 and M1 are on, is reduced as if there is one transistor $V_{th}$ less to the supply voltage and thus less energy is wasted during slow digital state transitions. A secondary benefit of this dual transistor structure layout is that no transistor gate is directly electrically connected to the input node IN. Transistors M4 and M5 in FIG. 8 do not play any part in the dual transistor structure upon the input. Further, with only transistor source contacts connected to outside of the electronics module the design is also more robust against ESD damage.

6. Body Contact Cross-Coupled Transistor Stack Pairs

At a high level the underlying concept described within the following detailed description within this section can be applied to any pair of matched transistors in order to boost their effective drain impedance significantly, to around infinity in general and in some regions into the realm of negative impedance. Applications of this inventive concept include, but are not limited to:

A) Current mirrors/references where figures of merit for such circuit elements are defined by how little overdrive does the current mirror need to reach its saturation (high-impedance) region and how flat is the current response for any given voltage, i.e. how high is the impedance; and B) Operational Amplifiers (OpAmps) where the concept unlocks very high gain and very high energy efficiency.

The inventive concept is based upon two core ideas:

1) Stacking a pair of transistors of same voltage threshold and connecting the bulk and gate contacts together for the transistor on the drain-side of the stack while the transistor on the source side has its well contact connected to its source or ground; and 2) Adjusting the body contacts to create a bias-less cascode-like transistor structure with much higher output impedance.

One trade-off for the inventive concepts is that they cannot be employed with a large $V_{gs}$. Essentially, the inventive concept is for near-threshold transistor operation.

6A. Overview

Figure 9B:
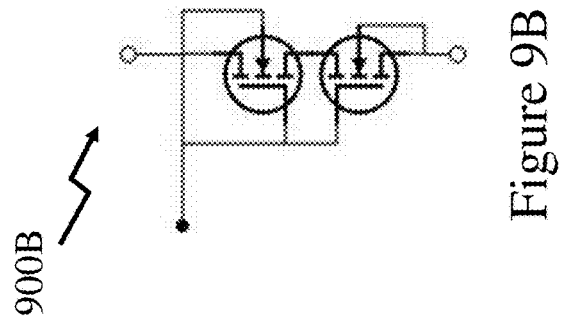
FIG. 9B depicts a "compounded MOSFET" according to an embodiment of the invention.
Figure 9A:
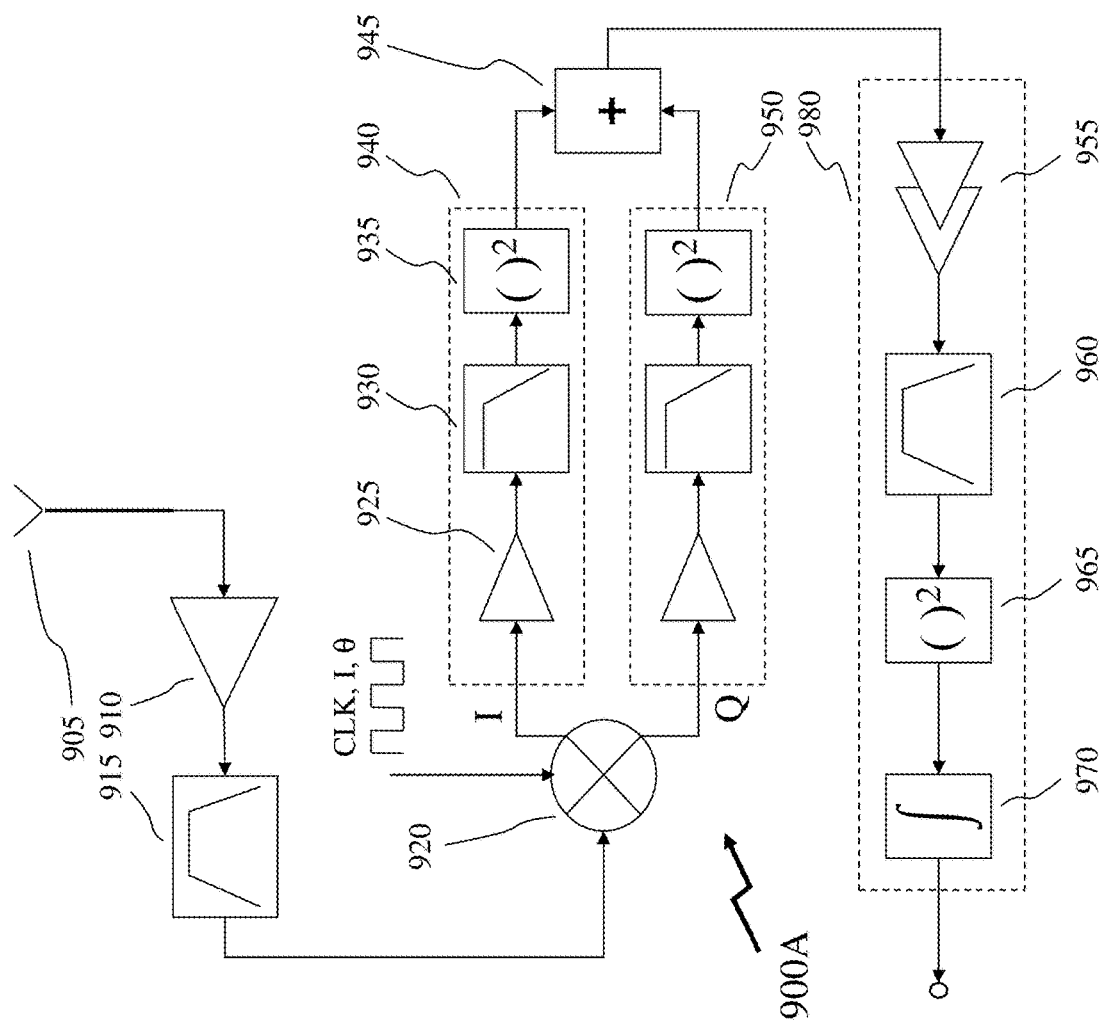
FIG. 9A depicts a UWB receiver according an embodiment of the invention.

Referring to FIG. 9A there is depicted a UWB receiver 900A according an embodiment of the invention allowing the UWB receiver 900A to detect pulses received by an antenna 905 which have been transmitted by a transmitter according to an embodiment of the invention. Accordingly, the antenna receives a pulsed UWB signal, which consists of a carrier signal that is pulsed according to a fast envelope. This received signal is coupled initially to a Low Noise Amplifier 910 which amplifies the signal wherein the amplified signal is bandpass filtered by first filter 915 to suppress out-of-band interferers. Optionally, other amplifiers can be present at this RF stage prior to mixer 920. First filter 915 may, for example, be a bandpass filter.

Next, an in-phase quadrature mixer 920 multiplies the received filtered and amplified signal with a square clock, thus down converting the pulses to an uncertain intermediate frequency, IF1, where the IF1 frequency is the difference between the pulse carrier frequency and the clock frequency. As the UWB receiver 900A is an energy receiver the paths in quadrature are required (90 degrees out of phase) such that the total energy of the pulse is preserved where the in-phase, I, and quadrature signals, Q, are split between the two paths in accordance with the phase difference between RF signal and clock. Even if UWB Receiver 900A was not an energy receiver both paths would be required to avoid the scenario of using a single path, either I or Q, and the received RF signal and clock being out of phase to yield no signal in the single path.

The IF1 signals within the I and Q arms are processed by first and second signal processing circuits 940 and 950 respectively. Each of these comprises an amplifier 925 such that the mixed and down converted IF1 signals are amplified and these are then filtered by a second filter 930, for example a sharp low pass or bandpass filter, which is established in dependence upon a UWB band upon which the receiver is currently operating. The output of each second filter 930 is then squared by a squaring operation performed by first squarer 935 in order to extract the instantaneous power on that path. The outputs from the first and second signal processing circuits 940 and 950 respectively are summed into the total instantaneous power by summation circuit 945.

The output of the summation circuit 945 is then coupled to an amplification stage 955. This amplified signal is then filtered by third filter 960, squared by a squaring operation performed by second squarer 965 and then integrated with integrator 970. The amplification stage 955, third filter 960, second squarer 965 and integrator 970 forming a third signal processing circuit 980.

The signal from summation circuit 945 follows the envelope of the pulse signal with the RF carrier removed. Accordingly, without knowing the exact pulse carrier frequency, it is still possible to receive the signal whilst applying sharp filtering. The amplification within each of the first and second signal processing circuits 940 and 950 together with that of the third signal processing circuit 980 may be fixed gain amplifiers or variable gain amplifiers. In embodiments of the invention where variable gain is employed then this can be employed to amplify the signal to full strength which in conjunction with the bandpass filtering allows removal of narrowband interfering signals.

The amplifier 925 within each of the first and second signal processing circuits 940 and 950 respectively is required to amplify the low signal from the mixer 920 for subsequent processing. Accordingly, for UWB receivers according to embodiments of the invention the amplifier 925 has performance requirements such as those listed below in Table 2. Within the following description there is described the implementation of amplifier 925 using an operational transconductance amplifier (OTA) intended for a commercial foundry CMOS process exploiting 0.13 µm technology.

TABLE 2

| Target OTA Performance | | |
|---|---|---|
| Parameter | Value | Unit |
| Supply Voltage | 1.2 | V |
| Common Mode Voltage | 0.5 | V |
| Output Load | 500 | fF |
| DC Gain | >60 | dB |
| Harmonic Distortion | <0.2 | % for 600 mVpp input (unity gain configuration) |
| Input Referred Power Spectral Density (PSD) Noise | <100 | nV/$\sqrt{Hz}$ @ 1 MHz |
| Static Power Consumption | <200 | µW |

An additional design goal was to establish dominant Laplace poles at approximately 10 kHz and 100 MHz in open-loop configuration although the actual pole locations are only guideline rules as the only real requirements for this criterion are stability and the equivalent gain-bandwidth (GBW) product which should be above 10 MHz in this case. Additionally, the main criterion for establishing a relative figure of merit for the design is the power consumption making it a critical differentiating parameter. Within the following description this criterion and the absence of a strict silicon area requirement was the motivation for the design decisions for the OTA.

6B. Selected Operational Amplifier (Op-Amp) Circuit

It would be evident that there are different approaches to establishing a circuit fulfilling the criteria listed in Table 1. A traditional model of an OTA employed to meet these requirements would be a typical 2-stage amplifier with a PMOS differential input pair joined with an NMOS current steering mirror and followed by a simple common-source NMOS voltage amplifier. However, using multiple stages on different current branches involves the consideration and placement of at least two poles which are already specified in the list of criteria and involves the use of passive components for compensation and the resulting stability concerns for the design. Trying to push the pole of the last stage of such a 2-stage amplifier requires reduction of the output resistance as much as possible since the output capacitance should be at least 500 fF. Since the output pole's frequency follows the simple RC constant law given in Equation (1) then for the second pole to be at least 100 MHz (i.e. $\omega_{p2}$=628.3 Mrad/s) and the capacitance ought to be at least 500 fF with some additional capacitance from the drains of the output transistors, $R_O$ must be below 3183Ω which implies serious constraints on a power limited design.

$$\omega_{p2} = \frac{1}{R_O C_{load}} \quad (2)$$

An output impedance of 3 kΩ implies that the output current must vary (linearly) by 1/3000 amp for each volt that the output node charges or discharges. Considering that the supply voltage is 1.2V, the output current must therefore vary by approximately 400 μA from rail to rail. This is not physically possible without a nominal current source of 200 μA of static current at the minimum which would produce at best a sourcing current of 200 μA when the final settling voltage is 0.6 V and the starting voltage is 0 volt. The gain of the last stage would have to be so low that the PMOS used as a current source for the last stage would have to be replaced by a resistor and even then, the required static current of 200 μA entails a static power consumption of 240 μW which alone exceeds the entire power budget for the OTA. Faced with the impossibility to simultaneously meet the target criteria in Table 1 with a traditional op-amp design, new architectures had to be explored that could meet all these criteria.

The simplest and most straightforward adaptation of the traditional op-amp that could help meet the speed requirement is the insertion of a common-drain as a third stage in between the 500 fF load and the last voltage amplifying stage which would result in a much lower output impedance for a given current. Through early simulations, it was possible to bring down the required current to around 40 μA for each of the two last stages which ensured that the combination of performance criteria with respect to pole frequencies and static power consumption were not out of reach anymore. However, the highly non-linear impedance of the output of the common-drain stage is suitable for a voltage operational amplifier but not an operational transconductance amplifier as required. The difference between the two is the nature of the output signal; one is a voltage, the other is a current and thus the current response must be more or less linear for at least half the supply voltage. Furthermore, with the common-drain stage, there are three poles to place instead of two which further complicate the stability requirements in unity-gain configuration.

One way to solve all the multi-pole instability issues and the power requirements that necessarily come with it is to design the OTA out of a single current branch. To do so, the OTA would have to be made of a single differential pair but would only have one dominant pole. Thus, this pole would have to be set at only 10 kHz as the only dominant pole instead of 100 MHz as a secondary pole which makes a world of difference both in power requirement and acceptable capacitive load. Furthermore, no passive compensation network is needed for stability, in principle. The requirement of a pole at 10 kHz with a minimum DC gain of 60 dB stems from the need for a gain-bandwidth product of at least 10 MHz. This value becomes the transition frequency of the system and with the capacitive load, the biasing current of the differential pair is narrowed down to a limited range of values from which the preliminary design can be developed. The transition frequency is always defined by Equation (2).

$$\omega_t = g_m/C_{load} \quad (3)$$

Accordingly, with $C_{load}$ slightly larger than 500 fF due to the parasitic capacitance of the OTA itself and a $\omega_t$ significantly above 62.83 MHz (2π×10 MHz), a $g_m$ of 40 μA/V is sufficient. This transconductance figure can be obtained with a total biasing current below 5 μA for the differential pair due to the sharp current transfer function of MOSFETs in subthreshold operation. However, as a result of concerns with respect to noise constraints and distortions, the incremental search for an optimal design was started with a biasing current of 8 μA.

When building everything out of a single current branch a new difficulty arises. The DC gain which was easily obtained with two cascaded stages now becomes much more challenging with only a differential pair and 1.2 volt of supply voltage. To further complicate matters, half of the supply voltage range must fall within the linear range of operation of the output and cap OTA distortion below 0.2%.

There is essentially a single approach for multiplying the gain of a transistor beyond what is possible with a very long MOSFET channel when its $g_m$ is fixed and that is by increasing its effective drain impedance, which is what a cascode does. However, traditional cascode structures offer very little voltage swing in low voltage processes since they have prohibitively high overdrive voltages. Furthermore, traditional cascoded stages need additional bias voltages that in the case of a differential pair must be different to the input signal and yet must follow closely the common-mode voltage of the input signal to always have the maximum amount of output voltage available. A common compromise for the overdrive problem is to stack two or more transistors in series and connect them to share the same gate voltage. Whilst the overdrive voltage of this structure is not significantly higher than the overdrive voltage of its single transistor equivalent, the benefits of this technique are marginal and insufficient to meet the requirements of the target OTA. This ineffective increase in gain arises because only the transistor whose drain is directly connected to the output is not squarely operating in its triode biasing region; the drain-source voltage of all the other transistors of the stack are all too low. If multiple transistors of a same stack must share the same gate voltage, which will be necessary for the differential pair of the OTA, the benefits of stacking transistors will inevitably be limited by this previously described effect unless they all have different voltage thresholds. Therefore, it is a convenient and common practice to connect in series the drain of a first transistor to the source of a second transistor with lower voltage threshold than the first one. In this case, the drain-source voltage of the first transistor is much higher allowing it to operate in or near its saturation region and reap most of the benefits of cascoding with no additional bias voltage needed and little extra overdrive to the structure.

However, this method uses an additional photolithographic mask for an extra doping step that often has high variability and will cause the difference in threshold voltages between the transistors of the multi-$V_t$ stack to vary significantly which in turns makes the cascode performance unreliable and more expensive to manufacture. However, an alternative to this is for all transistors to be operating in low overdrive voltage which allows for shifting the voltage threshold of any transistor in a stack precisely and reliably: There are multiple uses for the body contact of a transistor most of which involves the back-gate effect. This effect produces a shift in voltage threshold and connecting two transistors as depicted in FIG. 9B, referred to by the inventors as a compounded MOSFET 900B, allows for the creation of a compounded MOSFET structure whose effective gain and output resistance exceeds any single transistor irrespective of length. Polarizing transistors this way does induce forward polarisation of p-n junctions in the second transistor but because the bias current is at all times limited to very low values in the conditions where this structure will be used, this forward voltage is rarely above 0.2 volt and the junction leakage is often below or around the same magnitude as the gate leakage of the same transistors and therefore has no negative impact on the circuit performance. As depicted in FIG. 9B the compounded MOSFET is comprised from a pair of N-channel MOSFETs.

Figure 10:
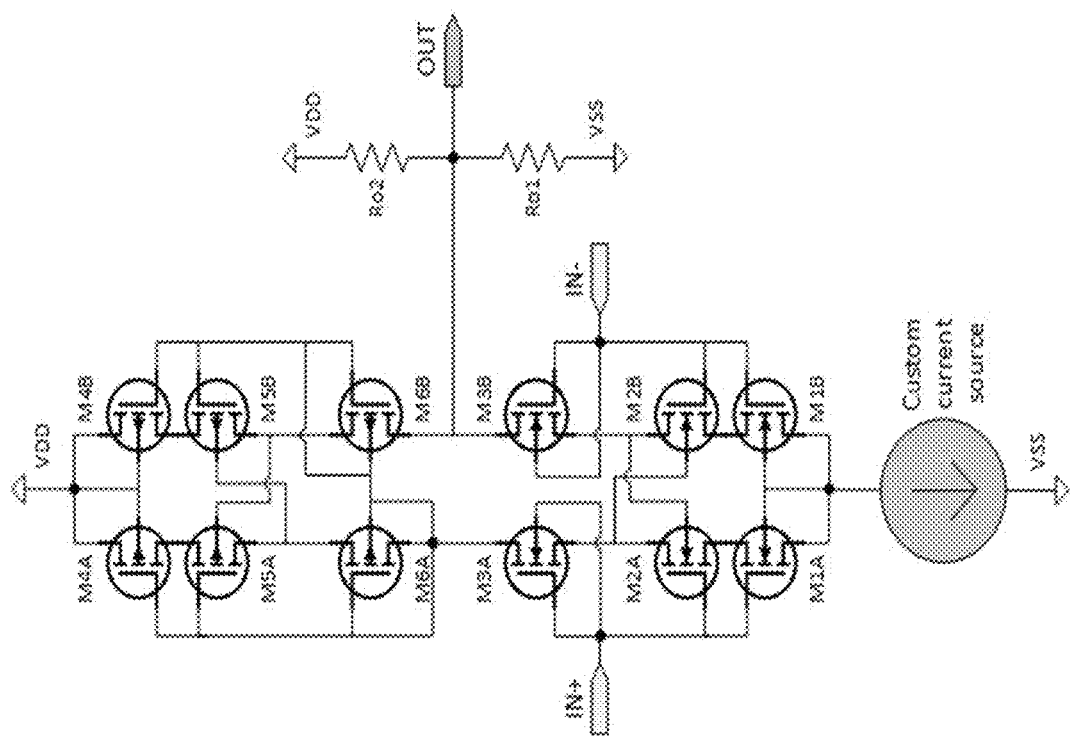
FIG. 10 depicts a schematic of a current mirror employing the compounded MOSFETs of FIG. 9 according to an embodiment of the invention.

This has been proven by the inventors through simulation to be effective at raising the effective gain and output impedance but substituting each single transistors of the OTA differential pair by its equivalent in FIG. 9B still results in an OTA that falls short of the target 60 dB gain requirement. Accordingly, this compounded MOSFET 900B can be adjusted further to increase the gain significantly without any significant increase in minimum drain-source operating voltage. This adjustment is only possible for transistors that are somehow paired with another identical transistor which works for both the differential pair and any current mirror. Accordingly, to further increase the drain impedance of the compounded MOSFET 900B in FIG. 9B without increasing its minimum channel operating voltage, a third transistor is introduced into the stack in the middle position where its body-source bias voltage also must be between the body-source bias voltages of the two other transistors already in the stack. In order to achieve this, the inventors tie the body contact of the middle transistor to its drain and since its drain voltage is not much higher than its source voltage because they are squeezed between the two other transistors, the body-source junction voltage of the middle transistor is also not high enough for any significant leakage. However, tying the body contact to the drain of the same transistor makes it behave weakly like a diode-connected transistor since the body contact behaves like a weak gate and diode-connected transistors do not present a high impedance through their drain which defeats the purpose of having a third transistor in this case. This is where paired transistors come into play and the disadvantage of the diode-connected effect is turned into an advantage. Because paired transistors are meant to behave relatively to one another, connecting the body contact of a middle transistor to the drain of the middle transistor on the opposite side of paired transistor stacks as depicted in FIG. 10 causes the diode-connected effect to work in favor of a higher drain impedance rather than against it.

For the current mirror of FIG. 10 it acts in the following manner to a change in drain voltage. An increase in drain to source voltage of the transistor M6B induces a slightly increased current response of this transistor up until its source voltage also drops because M5B and M4B don't provide the same current at this very instant. Up to this point, this is the principle behind every cascode branch. This slight drop in absolute source voltage of M6B involves directly an equal increase in body-source voltage of transistor M5A which has the effect of slightly reducing the effective voltage threshold of M5A and slightly increase its conductivity. Thus, when the conductivity of M5A increases, the current flow in the transistor stack M4A to M6A momentarily increases until its gate-source voltage which is diode-connected decreases to compensate for it which in turn equally decreases the gate-source voltage of the transistor stack M4B to M6B. Thus, an increase in drain-source voltage of the output side of such a current mirror should induce a proportional decrease in the gate-source voltage of the whole current mirror and compensate for the channel modulation effect of the transistor M6B and allow the transistor stack M4B to M6B to present an effective output impedance much closer to infinity. In fact, the inventors have established experimentally that this output impedance can even be negative given the correct device dimensions. The same general ideas have been employed for the differential input pair as depicted in FIG. 10 and works on the same basic principles. The dimensions of the transistors within an exemplary embodiment of the invention are presented below in Table 3.

TABLE 3

Exemplary Transistor Parameters for OTA

| Transistor | M1 | M2 | M3 | M4 | M5 | M6 |
|---|---|---|---|---|---|---|
| W(μm) | 96 | 200 | 192 | 128 | 80 | 160 |
| L (nm) | 240 | 300 | 400 | 120 | 120 | 360 |
| # fingers | 8 | 8 | 8 | 8 | 8 | 8 |
| Transistor | M7A | M7B | M8A | M8B | M9A | M9B |
| W(μm) | 32 | 4 | 32 | 4 | 48 | 6 |
| L (nm) | 200 | 200 | 310 | 310 | 410 | 410 |
| # fingers | 16 | 2 | 16 | 2 | 16 | 2 |
| Transistor | M10 | M11 | M12 | M13 | M14 | M15 |
| W(μm) | 4 | 4 | 2 | 2 | 2 | 2 |
| L (nm) | 300 | 300 | 300 | 300 | 500 | 500 |
| # fingers | 4 | 4 | 2 | 2 | 2 | 2 |
| Transistor | M16 | M17 | M18 | M19 | | |
| W(μm) | 16 | 16 | 4 | 4 | | |
| L (nm) | 500 | 500 | 300 | 300 | | |
| # fingers | 16 | 16 | 4 | 4 | | |

The decision to use an NMOS differential pair instead of a PMOS was based upon the fact that there is no second current branch to this OTA and NMOS performances are better and the necessary drain-source voltages to achieve linear behavior have been found to be lower with NMOS through simulation. Therefore, a differential pair comprises NMOS transistors is part of a current branch that put two NMOS transistors and only one PMOS transistor in the current path whereas a PMOS differential pair would be in the reverse situation and, in principle, require a higher operating voltage.

Figure 11:
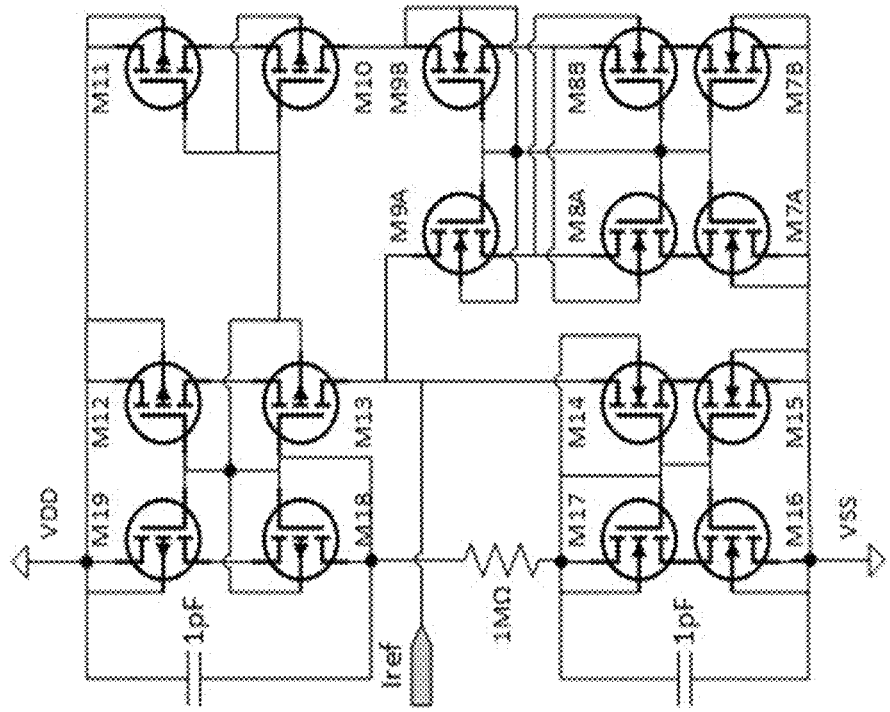
FIG. 11 depicts a full circuit schematic of a custom current source including reference circuit according to an embodiment of the invention.

Accordingly, a full circuit schematic of the custom current source including reference circuit is depicted in FIG. 11 which also uses the same concepts inspiring the design of the differential pair as they are suitable for most low polarisation low-speed transistor applications. This provides for a current reference that has an excellent output resistance and a very small minimum operating voltage which wouldn't be possible with any state-of-the-art current mirroring circuit. Table 2 above lists each MOSFET's dimensions for both circuits of FIGS. 10 and 11 where instance names M1 to M6 refer to both units with suffixes A and B which are matched and meant to be identical and therefore holds the same values in the table. "W" refers to the total width.

6C. Current Source Analysis

In order to benefit from the largest input and output voltage swing necessary to achieve a good total harmonic distortion (THD) figure, the current OTA must have the smallest minimum operating voltage. On the other hand, to benefit from the best common-mode rejection ratio which also can cause distortion, the same current source must sink a current as constant as possible across its output voltage which is synonymous with the highest impedance. These two conflicting requirements involves the need for a high quality current source.

The current entering the $I_{ref}$ terminal of FIG. 11 is mainly sunk by the transistor stack M7A to M9A through the same kind of compounded MOSFET structure that is now the signature of this OTA. However, it was discovered through simulation that the most "linear" current response to output voltage with the lowest minimum operating voltage is not the flattest response (closest to an infinite impedance). In other words, the device parameters that cause the impedance to be constant over the widest voltage range is not the highest possible impedance but fortunately a negative impedance of approximately −20 MΩ. Therefore, it was possible to put in parallel with the main current source of −20 MΩ current branches that presented a total of +20 MΩ when connected to the output and since the current branches do not have to provide the same current as the main current source but can be much smaller current sources, achieving an impedance of −20 MΩ is not difficult. Those secondary current sources sink around 95 nA through transistor M14 and source around 400 nA through M13 and those currents vary slightly to compensate for the negative impedance presented by the drain of M9A which sinks around 7.2 μA.

Figures 12, 13:
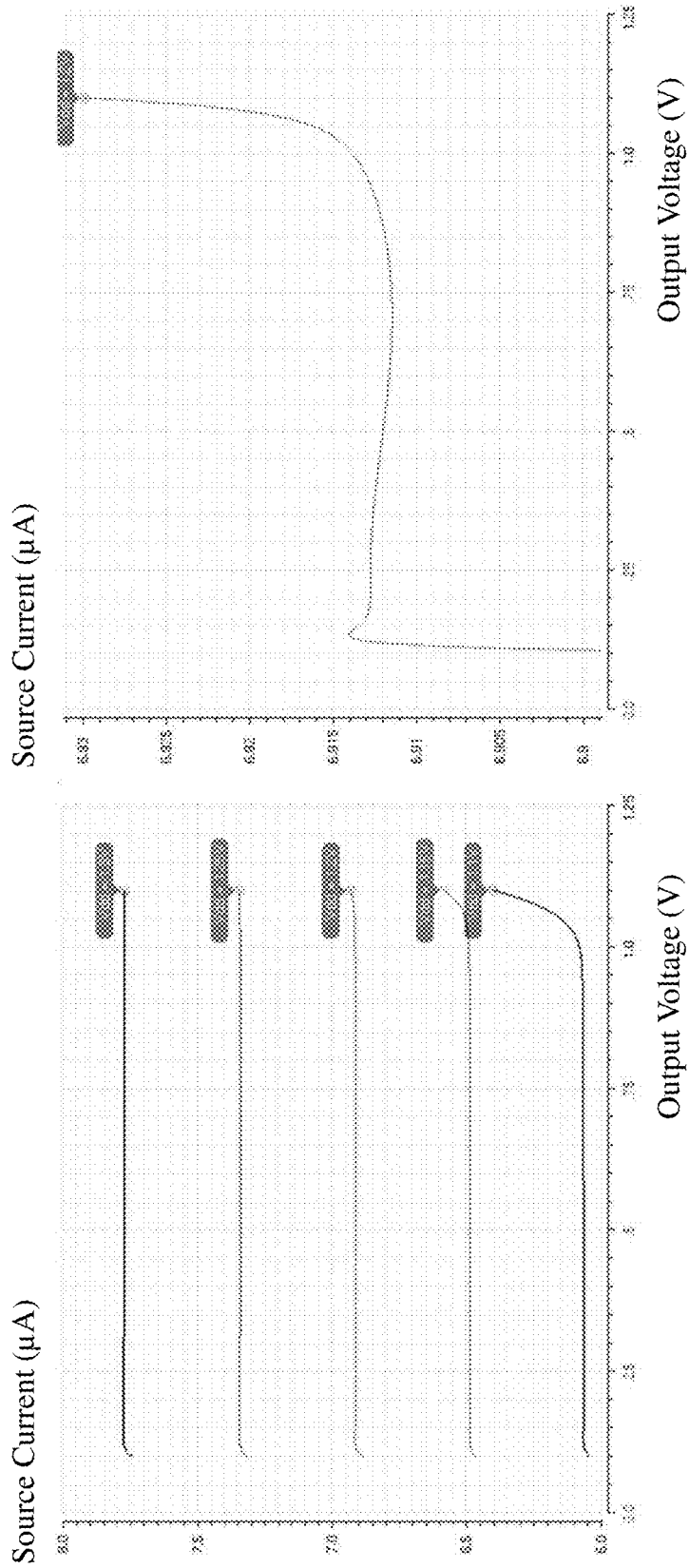
FIGS. 12 and 13 depict the spread along with the ultimately desirable "flatness" of the custom current source of FIG. 11 according to an embodiment of the invention.

During the evaluation of designs for the OTA a sensitivity of bias to external factors was not part of the scenarios. Transistors M16 to M19 along with a 1MΩ ideal resistor constitute a rudimentary source of bias that defines the current in all other branches of the whole OTA but doesn't vary too much across supply voltage spread. FIG. 12 illustrates the spread along with the ultimately desirable "flatness" of the custom current source at all values of supply voltage. FIG. 13 depicts the extent to which the current changes over output voltage and with less than 3 nA of variation (<400 ppm of the nominal current) from 120 mV to 1 V, this illustrates the high performance of this current source within 0.13 μm CMOS. The very low overdrive voltage is important to obtaining sufficient output voltage swing and a significant distortion figure at low frequencies.

6D. DC Analysis

Given that the ultra-high impedance structures that the customized current source is constructed from also constitute the whole OTA, the optimized MOSFET parameters put the OTA in a state where its output impedance is also negative. For this reason, resistors Ro1 and Ro2 in FIG. 10 have been added at the OTA's output to compensate for the negative impedance but are left at undefined values since their optimal values vary according to the gain factor β of the feedback path. However, for β=1 (in unity-gain configuration), the optimal resistive network impedance turned out to be around 15 MΩ with a neutral voltage of 0.3 V at which voltage the net current exiting the voltage divider is null. These two values imply Equations (3) and (4) for Ro1 and Ro2 under the desired supply voltage of 1.2 V.

$$\frac{1}{Ro1} + \frac{1}{Ro2} = \frac{1}{15M\Omega} \qquad (4)$$

$$3Ro1 = Ro2 \qquad (5)$$

Substituting "1/Ro1" by "3/Ro2" in the Equation (3) yields "4/Ro2=1/15 MΩ" which leads to Ro2=60 MΩ and Ro1=20 MΩ. Henceforth, unless otherwise mentioned, the total impedance of this voltage divider is Ro=15 MΩ by having Ro1 and Ro2 being 20 MΩ and 60 MΩ respectively for all simulation results.

Figure 14:
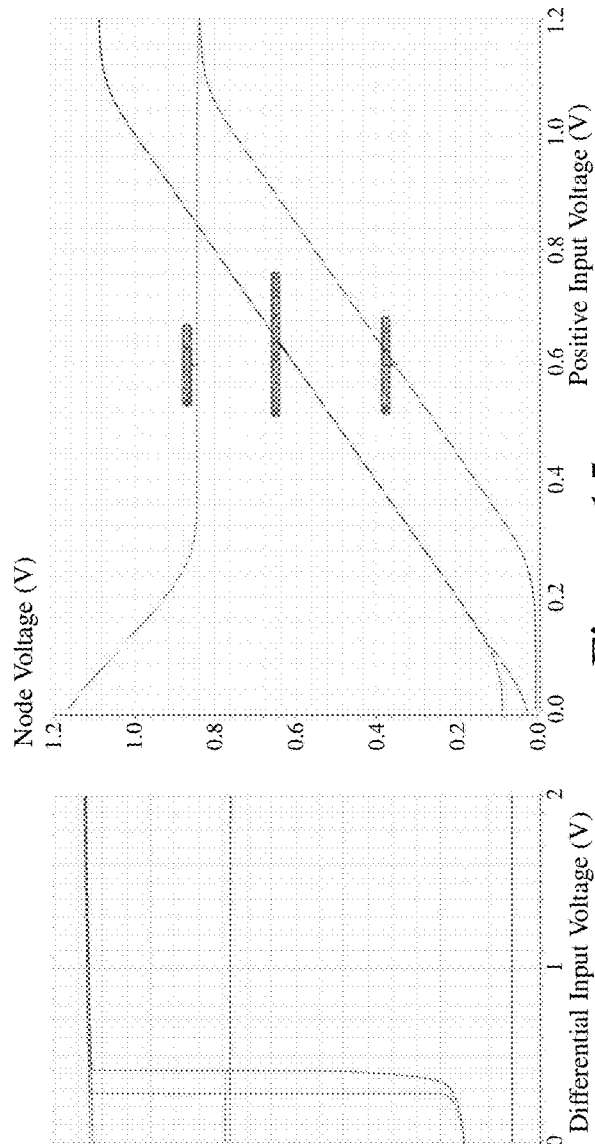
FIG. 14 depicts a hysteresis transfer function with respect to a small differential input signal from an operational transconductance amplifier (OTA) employing the compounded MOSFET as depicted in FIG. 10 according to an embodiment of the invention.

The OTA having a negative output impedance on its own in open-loop prevents its large signal transfer function to show a definitive identifiable DC gain. Instead, FIG. 14 depicts a hysteresis transfer function from a small differential input signal around Vcm=0.5V which fortunately only appears in open loop operation. This is because this OTA is not meant to operate in open loop because the design was executed with the assumption that the OTA would not need to operate in open loop. Whilst not defined as a criterion of the OTA design given that the desired open loop gain must be any value above 60 dB and not within a narrow range of values implies on its own that there ought to be some kind of negative feedback around the OTA for it to work as intended once integrated in another circuit and therefore, the aforementioned assumption is justified. Even without the compensation resistors Ro1 and Ro2, the hysteresis "opening" in the transfer function spans less than 2 millivolts of differential input signal and is completely suppressed even with weak feedback factors (β<0.01).

Figure 15:
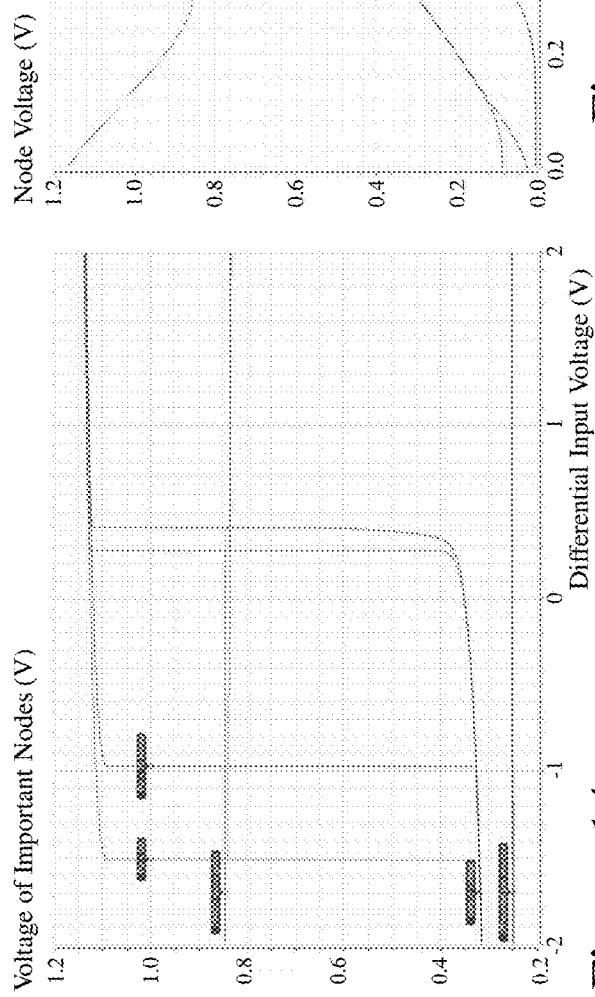
FIGS. 15 and 16 depict simulation results for an operational transconductance amplifier according to an embodiment of the invention in a unity-gain configuration.
Figure 16:
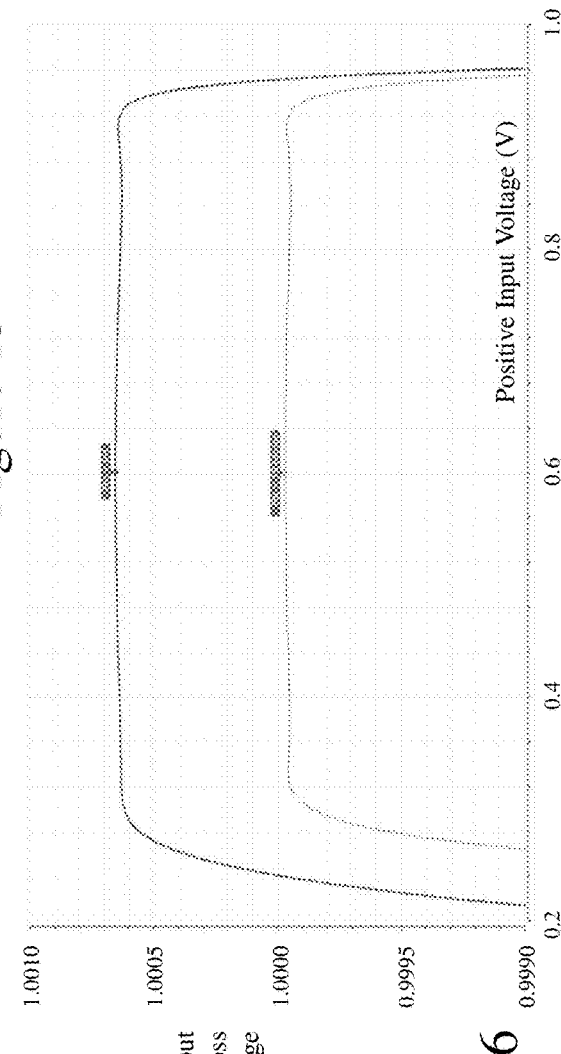

The two relatively constant voltages labelled "PMOS mirror gates" and "differential pair source" in FIG. 14 serve to provide a clue right away as to what is the available input common-mode range. Quick simulations at different common-mode voltages to the nominal value of 0.5 V showed that the hysteresis spread is insensitive to common-mode voltage, so the results of FIG. 14 hold true independent of Vcm as long as it is within the operating input voltage range. Further, FIGS. 15 and 16 present in much more detail as to how the OTA behaves in unity-gain configuration and what is the extent of its 'strict' and 'loose' operating ranges. The OTA enters its optimal operating range where current is maximized and stable somewhere past 0.3 volt of common-mode since the PMOS mirror gates voltage is constant past that point and the voltage of the source terminals of the differential input pair faithfully follows the variations of the input signals. This voltage range ends near 1 volt where the transfer functions of FIG. 15 inevitably start to curb down.

Furthermore, FIG. 16 allows us to pinpoint with much greater accuracy where exactly does the optimal operating range of the OTA starts and ends by plotting the derivative of the output curves of FIG. 15. It turns out that the compensation resistors reduce slightly this optimal range, but this comes at the benefit of an even more accurate reproduction at the output of the input signal since the curve "Ro=15 MΩ" is within 50 ppm of the ideal unity-gain transfer curve. Hysteresis effects aside, FIG. 16 implies an open loop gain in excess of 20 kV/V which is over 86 dB. This is simply obtained by isolating $A_{open\text{-}loop}$ in Equation (5).

$$\frac{A_{open\text{-}loop}}{(A_{open\text{-}loop} + 1)} \geq 0.99995 \qquad (6)$$

In scenarios where the emulated open-loop gain adjusted by the compensation resistors is not needed, the voltage range is somewhat wider without those resistors; at least from 0.3 to 0.92 V whereas the lower limit recedes to 0.32 V with 15 MΩ of output resistance compensation. This leaves just enough range for the half supply voltage sine wave required to evaluate distortion figures.

As for the effective offset, it cannot be pinpointed exactly only with the transfer function of FIG. 14 because of the hysteresis effects. Accordingly, FIG. 17 displays the voltage difference between both inputs for the exact same scenarios as in FIGS. 13 and 14. Predictably, the offset is a constant +0.4 mV over the whole optimal range with the 15 MΩ compensation.

6E. AC Analysis

Open-loop AC analyses may seem irrelevant without a stable DC bias point that is in the optimal DC transfer slope. However, for the sake of conformity with the requests of the assignment and for the gain-bandwidth product simulation which is still needed, a small-signal AC simulation was performed with a signal offset of 0.4 mV (and an output compensation resistance of 15 MΩ) to get to a reasonable bias point. These simulation results are depicted in FIG. 18 where the open-loop gain is 76 dB and the GBW is 25 MHz. The pole placement was not strictly respected but the low frequency pole of approximately 4 kHz that had to be at 10 kHz is more than compensated for by the very high DC gain and the GBW above 10 MHz. With the phase plot just under its corresponding magnitude it is possible to see that the phase margin is just under 74 degrees which is just over the ideal phase margin and is generally obtained with an OTA by virtue of it having only one main pole instead of two.

The power spectral density of the noise simulation is depicted in FIG. 19 indicating it produces results below the maximum tolerated for the target 100 nV/√Hz at 1 MHz.

6F. Transient Analysis

All transient analyses of this OTA were performed in the unity-gain configuration with a compensation output resistance of 15 MΩ. For the slew rate, FIG. 20 shows that the rise time (~20 ns) is much shorter than the fall time (~200 ns) which is opposite to the performances of a traditionally designed OTA. The slew rate of this OTA is also much slower which arises from the tradeoff that needs to be to achieve ultra-low current consumption figures anyway. Accordingly, a tradeoff between slew rate and power consumption is relatively straight forward considering the power consumption was designated as a main (and only) differentiating parameter whilst no constraint on slew rate was specified.

These slew rate figures also show the extent of the voltage swing as does FIG. 15. The main difference here is that FIG. 20 shows how fast a given voltage can be reached. Accordingly, we can reasonably expect an output signal to swing from ~25 mV to ~1.08 V without compensation resistors or from ~85 mV to ~1.08 V with 15 MΩ of compensation if there are no timing constraints. If there is, the lower bound can be raised up to ~0.2 V. This is always in response to a full supply scale input signal and discounting distortion.

TABLE 4

THD Results from Distortion Analysis

| Frequency (kHz) | 0.01 | 10 | 1000 | 10000 |
|---|---|---|---|---|
| THD (ppm) | 2.183 | 5.18 | 3214 | 301500 |

For distortion figures, Table 4 lists total harmonic distortion values at key signal frequency points when the signal is a 600 mVpp sine wave centered at 620 mV. The value at 10 Hz serves to show that the DC transfer function's contribution to distortion is negligible and that only high frequency effects are responsible for distortion. The THD at 10 kHz is the one most interesting for the work since THDs count the most near the edge of the op-amp's bandwidth in open-loop. Hence, the nominal THD figure, the one that counts for the OTA's criteria is about 0.000518%. Despite the open-loop bandwidth being below 10 kHz, the intended bandwidth and the frequency of interest for the THD remains 10 kHz. Such a small figure is explained by the very high gain of the OTA itself even with compensation resistors. As far as the two last data points go, they show that in absence of sufficient gain and slew rate, THD figures degrade dramatically.

6G. Summary

A potential limitation of this OTA is the output voltage range can be variable and limited to the input common-mode voltage but fortunately, this is not always the case. In unity-gain configuration, it is not physically possible to pull the output voltage below the input voltage because it is directly connected to it and hence the OTA yields an excellent THD figure in this configuration. It is evident that the resulting OTAs from the different candidate topologies exceed the minimum requirements at a moderate cost in silicon area even though this was not a design parameter.

7. Biasless Low Power Differential (Exponential) Transconductance Stage

This innovative concept consists of generating a differential current from the voltage difference between two inputs alone.

Figure 21:
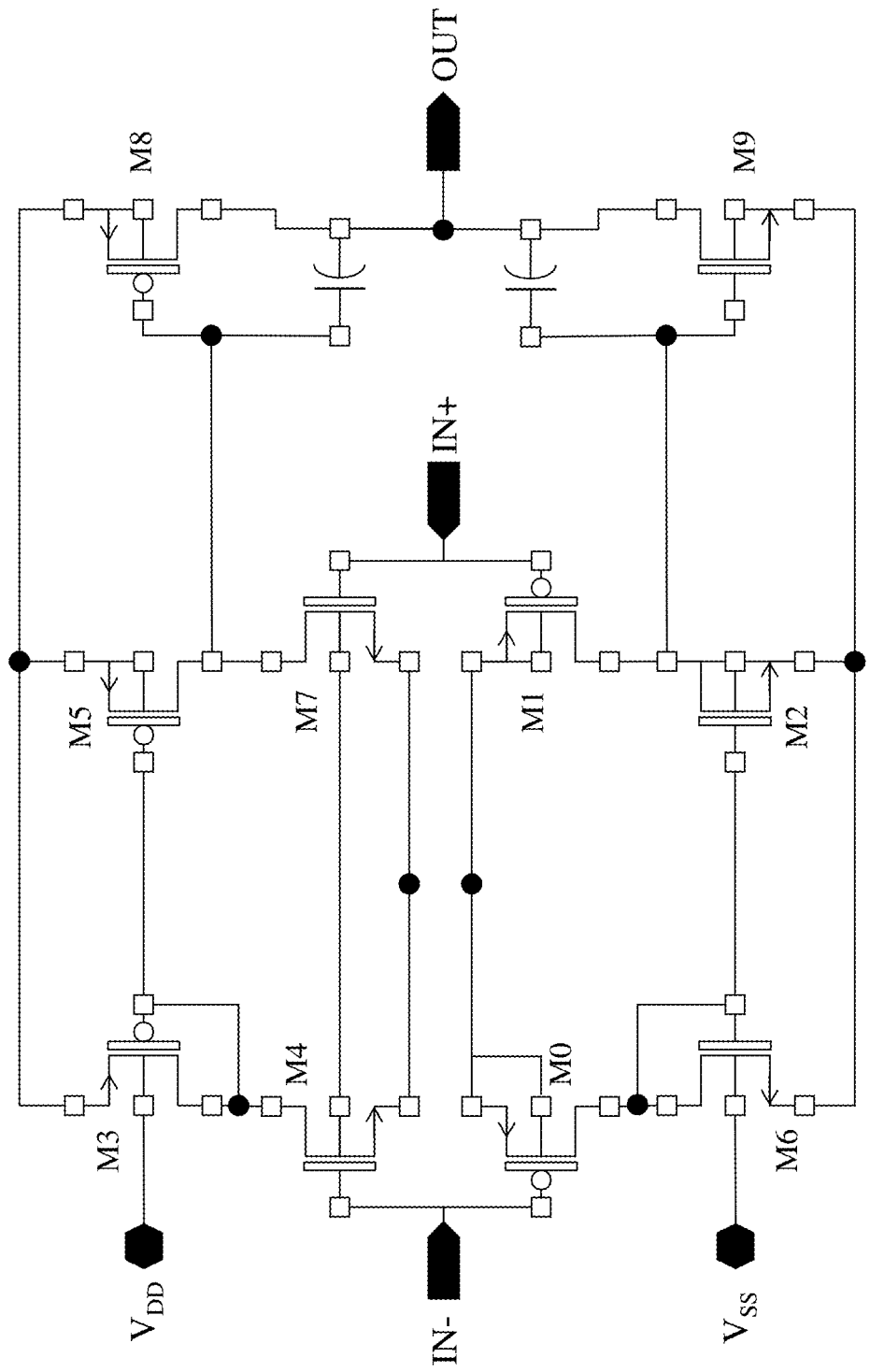
FIG. 21 depicts an exemplary schematic of an operational amplifier employing a biasless low power differential (exponential) transconductance stage according to an embodiment of the invention.
Figure 24:
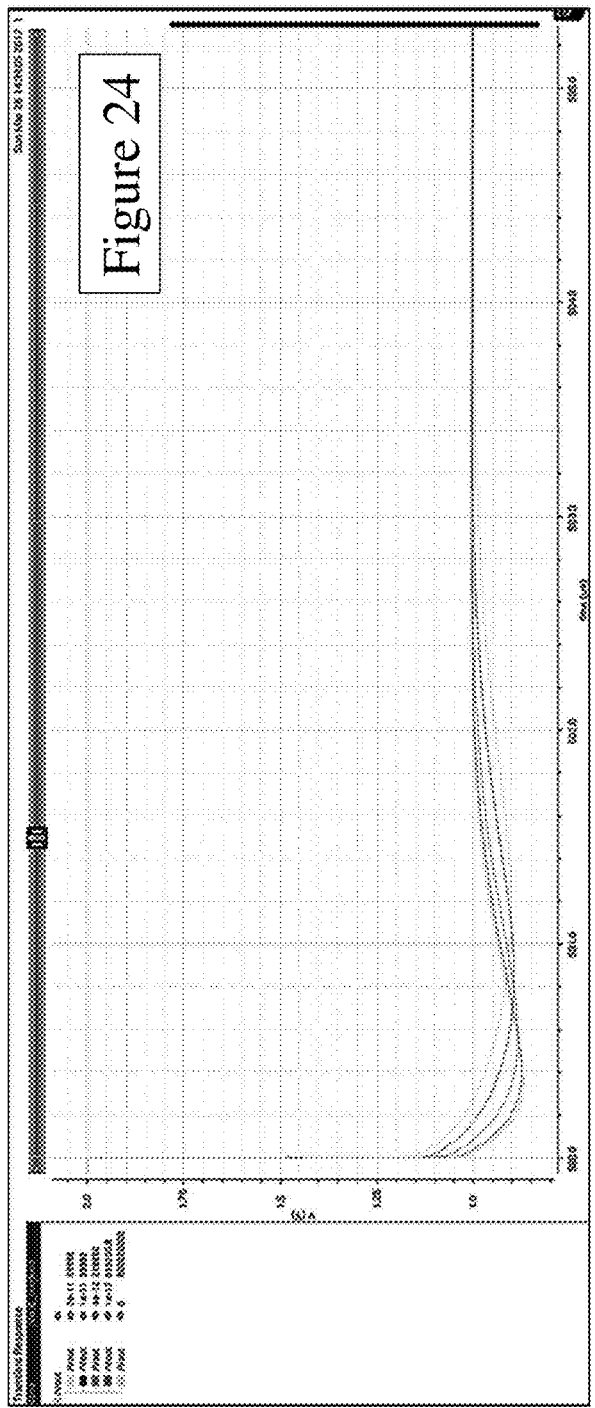
FIGS. 24 to 27 depict transient operation results for the operational amplifier employing a biasless low power differential (exponential) transconductance stage according to an embodiment of the invention as depicted in FIG. 21.
Figure 25:
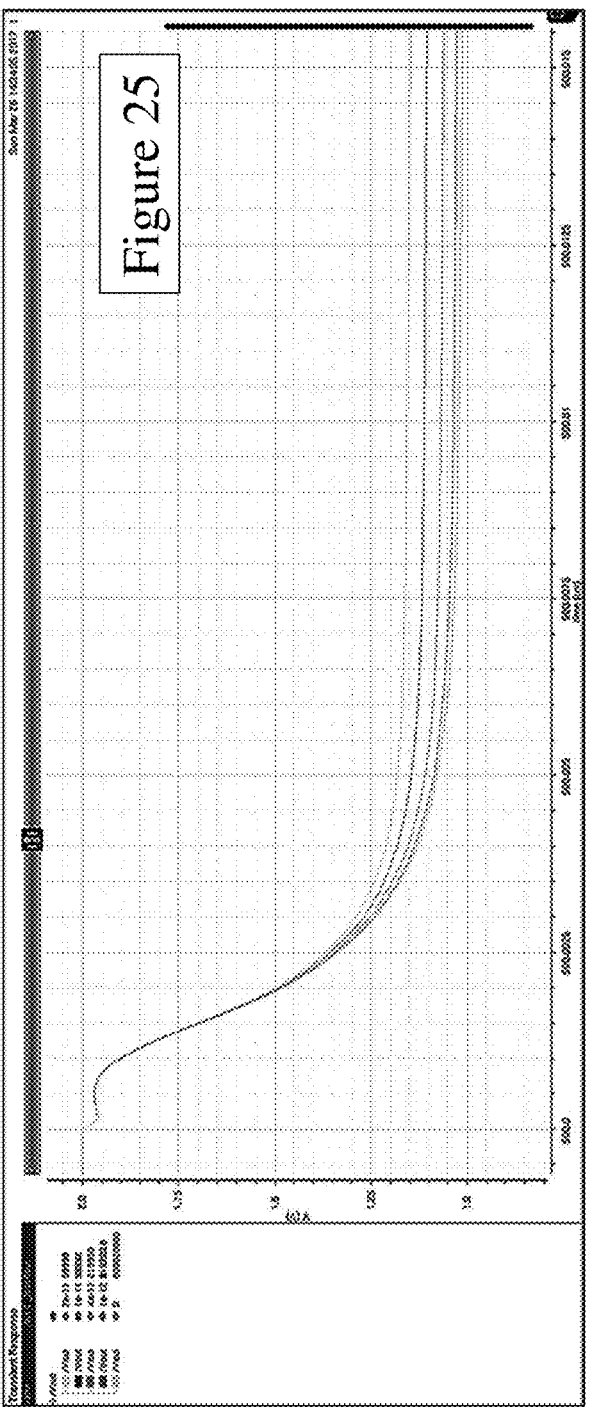

FIG. 21 depicts an exemplary schematic of an embodiment of the invention through transistors M0, M1, M4 and M7. Within FIG. 21 it is noted that the NMOS transistors are native transistors and thus still conduct when $V_{gs}$ is near 0 volts.

Figure 26:
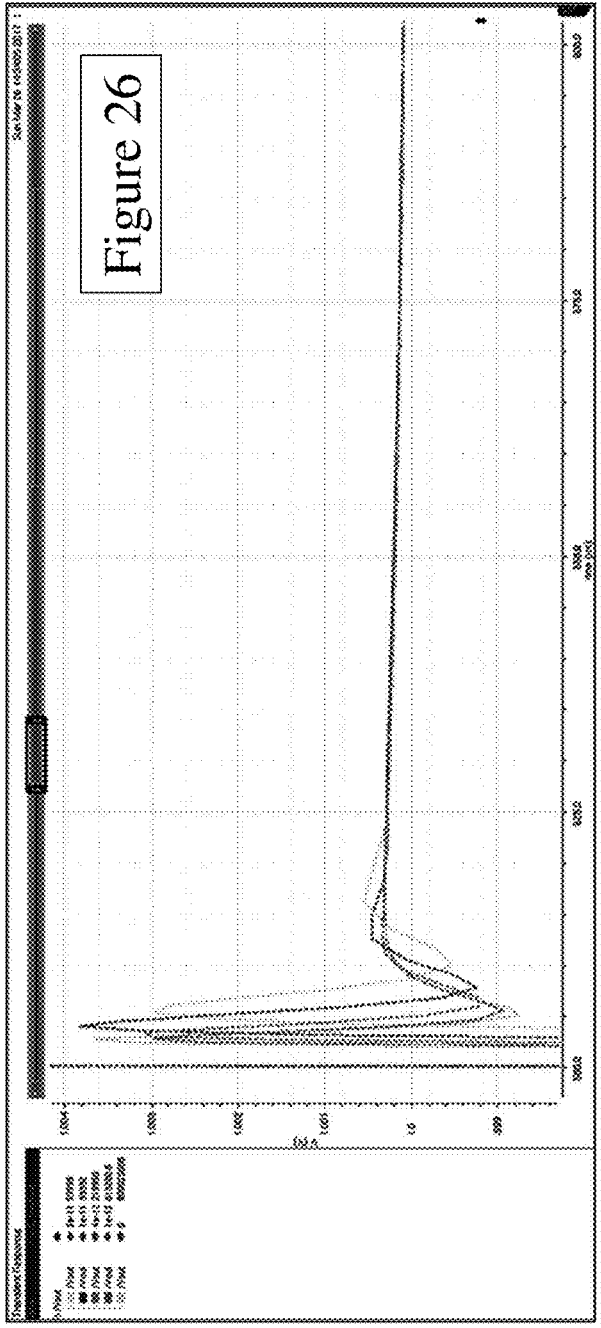
Figure 27:
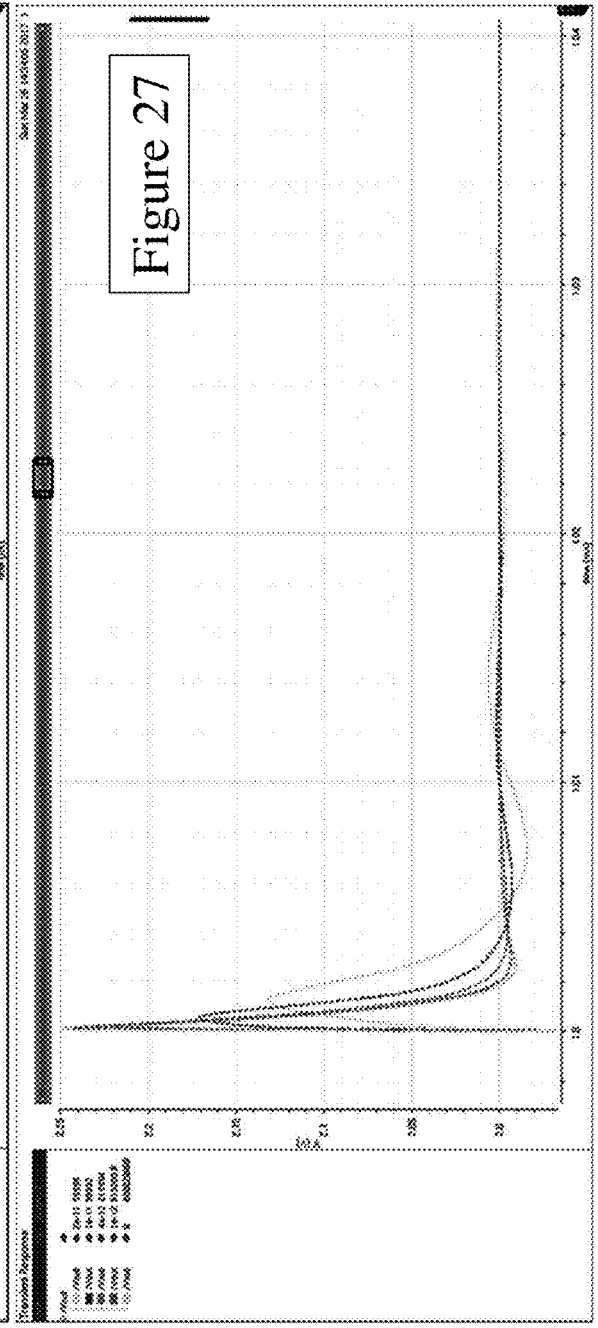

The circuit works similarly to two class AB power amplifying stages with their outputs shorted together. When one input has a higher voltage than the other one, the transistors it is connected to tend to pull the voltage up at their source where the NMOS transistors will conduct a little more current and the PMOS transistors will conduct a little less. The opposite happens for the input with less voltage in such a way that if the transistors are perfectly matched, the PMOS of one input will always sink the exact current the NMOS of the other input source. If this symmetry exists, then in a first configuration all four transistor sources can be shorted together as it is with the central node (net023) of the FIG. 26 because the voltage between all four of them would be the same anyway. In a second embodiment of the invention the source of M4 is connected to the source (and bulk) of M1 only and the sources of M7 and M0 would be part of a separate node.

Within an embodiment of the invention this configuration can be implemented within the OpAmp depicted in FIG. 21. This performs in the following manner: when the positive input has higher voltage than the negative input, the current in transistors M4 and M1 become negligible while the currents in M7 and M0 rise exponentially which pulls node net15 down and node net07 up and starves the PMOS current mirror and overfeeds the NMOS current mirror. Both net15 and net13 have lower voltages turning off the output NMOS and on the output PMOS.

The benefits of this idea over the state of the art in $g_m$ stages is first and foremost a very low quiescent current but provides a large gain and strong current response to a large voltage difference. Moreover, it does so without the requirement for a biasing circuit.

Figure 28:
FIG. 28 depicting the transient power consumption for the transconductance stage according to an embodiment of the invention in FIG. 21.

FIGS. 22 to 28 respectively depict simulation results for an embodiment of the invention, wherein these comprise:

FIG. 22 depicting DC transfer function with open loop DC gain=~85 dB with an input range between $V_{SS}$ +0.2V and $V_{DD}$ −0.7V;

FIG. 23 depicting continuous current results with maximum quiescent current of 500 nA with a typical current of only 6 nA when the output is saturated;

FIGS. 24 to 27 depicting transient operation wherein the non-linear current allows very steep transitions from 1V to 2V and vice-versa (large signal response) where the operational amplifier is optimized with a series resistance with the capacitive load; and FIG. 28 depicting the transient power consumption where the energy consumption is more efficient for a given load.

8. Native/Negative Threshold MOSFET Totem

Within exemplary UWB transmitter circuits, UWB receiver circuits, and UWB transceiver circuits according to embodiments of the invention a requirement exists for voltage references. However, prior art techniques such as employing a "bandgap" reference module current consumptions in the low hundreds of nA. Accordingly, it would be beneficial to provide a reference voltage source that only consumes a few nA. Exemplary embodiments of the invention exploit the ability of native (and depletion mode, i.e. negative Vth) transistors to conduct low but useable currents even when their $V_{gs}$ is negative.

The concept is based upon stacking native (or depletion) transistors along a "ladder" of electrical nodes from ground voltage level to as high as the highest reference voltage required for the circuit. If each node of the ladder is a "rung" numbered from 0 to N where node 0 is ground, then for native transistors, the electrical node of their gate is equal to i−1, the electrical node of their source is =i and the electrical node of their drain is =i+1 where i is the transistor number from 1 to N. Next a tunable current source is placed within the gap left within the current path between nodes (rungs) 0 and 1 because there is no −1 node for the gate contact of another native transistor. Tuning the current source allows for calibration of the voltage reference pulling more or less current through the transistor "ladder" which can be done digitally depending upon the design of the current source. It would be evident that the tunable current source may be implemented through a range of designs. Beneficially, the design is insensitive to power supply variations due to the significant transistor stacking as well as being insensitive to temperature variations as long as the current source is affected in a similar way to the native transistors within the ladder. Accordingly, all that is required is to calibrate out the process variation.

Considering the original problem then within the high voltage, i.e. 3.3V, digital domain transistors are large due to the requirement for large thick oxide transistors which are necessary to keep static current leakage to reasonable levels, ~100 s of nA instead of ~10 s of uA. Accordingly, the deep sleep power consumption is dominated by the bandgap voltage reference circuit and occasionally by activity on the serial to parallel interface (SPI) interface and the clock when employed. An initial approach to addressing this is to replace 3.3V input/output transistors with 1.8V input/output transistors which have minimum channel lengths almost half those of the 3.3 V transistors but still have the same $V_{th}$ resulting in the same low channel leakage.

Accordingly, in addition to reduce die real estate that also have lower parasitic capacitance therefore reducing the dynamic power consumption and propagation delays, the latter allowing the use of faster SPI clocks. Lower voltage swing and less charge required to charge a voltage node per unit of capacitance therefore reduce further the power consumption even if the digital circuit power supply is regulated through a linear regulator. Further, a lower voltage means the static current leakage is reduced as well. However, the operating voltage range of the chip must now be limited to ~1.8 V or it must be regulated for the thick oxide digital circuitry to allow a wide operating range (e.g. up to ~3.6 V).

Accordingly, without a voltage regulating solution that will only consume tens of nA of quiescent current or less, there is actually no saving on the overall energy budget and without appropriate care the design may even waste more energy with this solution. Beneficially, the requirements for the regulator are lax, namely:

Very low voltage precision required (it's supplying digital circuitry)

Very low current supply needed (up to an average in tens of μA when the wireless radio employs full speed SPI and modem operation.

Figure 29:
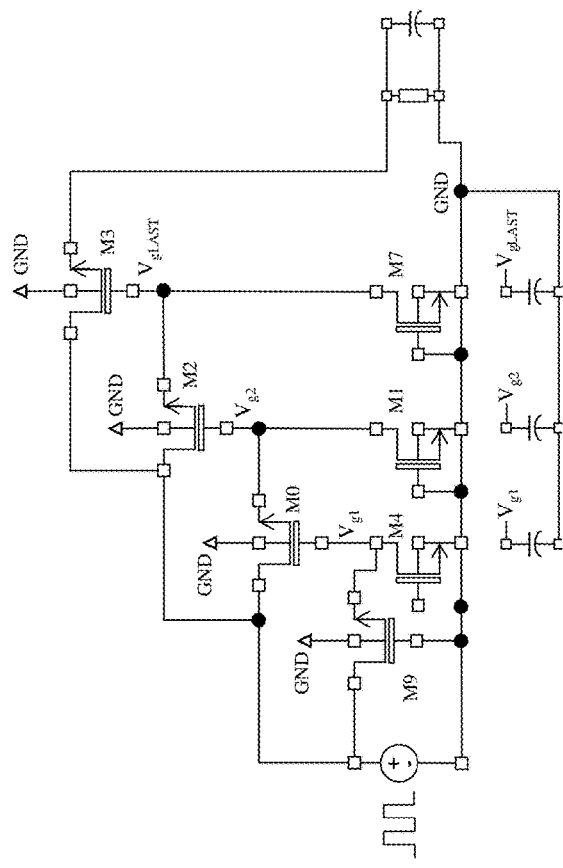
FIG. 29 depicts a MOSFET circuit according to an embodiment of the invention.

Initially, a discrete transistor was considered as drain current is insensitive to drain voltage when the transistor is in saturation and is best suited to being connected to an outside voltage source. Further, as the source has a very low impedance it is well suited to providing a wide range of current demands. Further, the source voltage can be pinned down within a few hundred mV by fixing the gate voltage. An exemplary circuit layout employing this concept is depicted in FIG. 29.

However, there are a few drawbacks of this simple solution, these being:

channel modulation effects add up with every additional stage;

temperature variations in the 0 to 85° C. range induce multiple orders of magnitude of current variations in sub-threshold transistors and tends to make the reference voltage vary significantly; and output voltage varies substantially with process variations! (~±40%)

Figure 30:
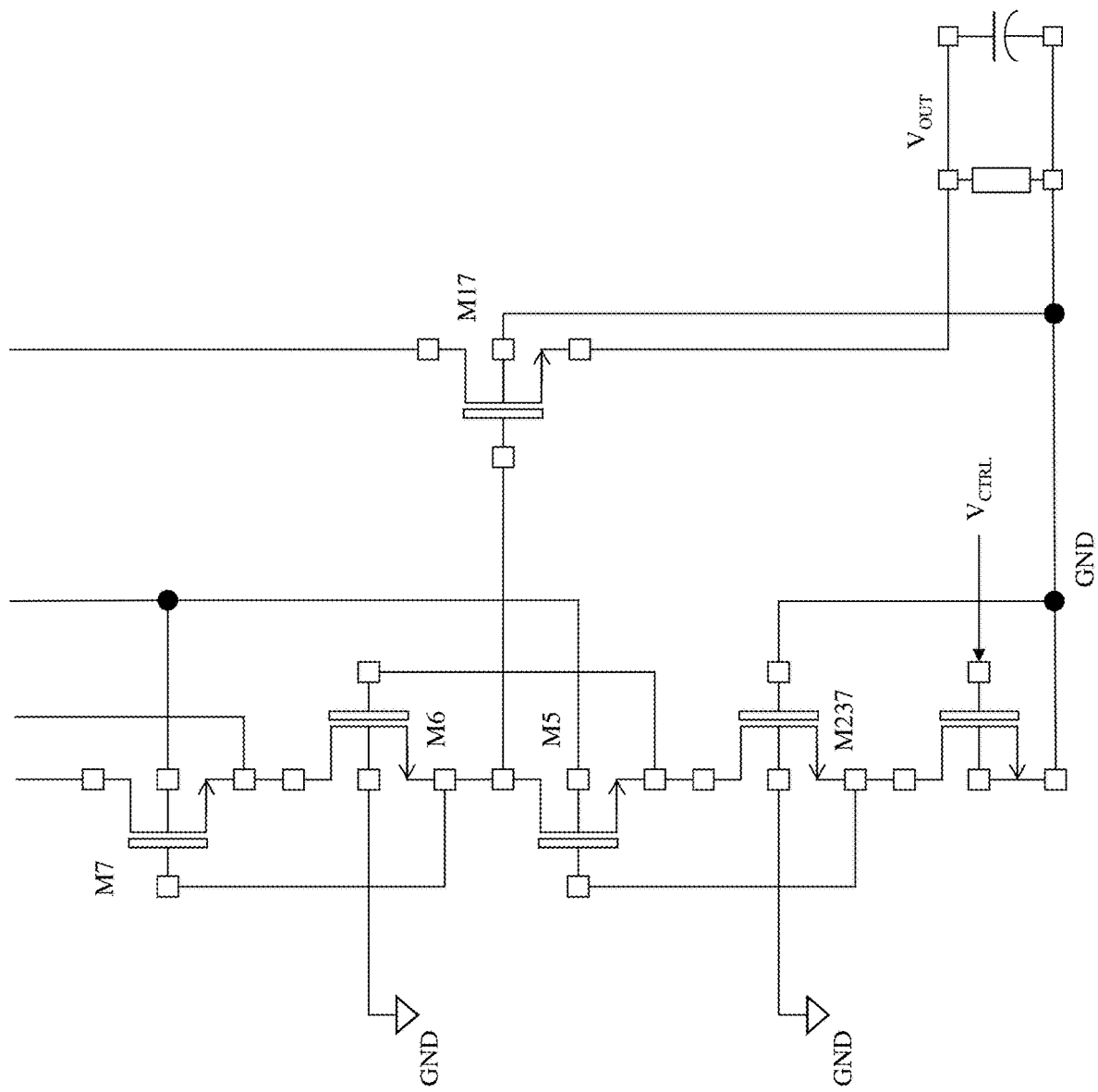
FIG. 30 depicts an exemplary circuit layout employing the native/negative threshold MOSFET totem according to an embodiment of the invention.
Figures 31, 32:
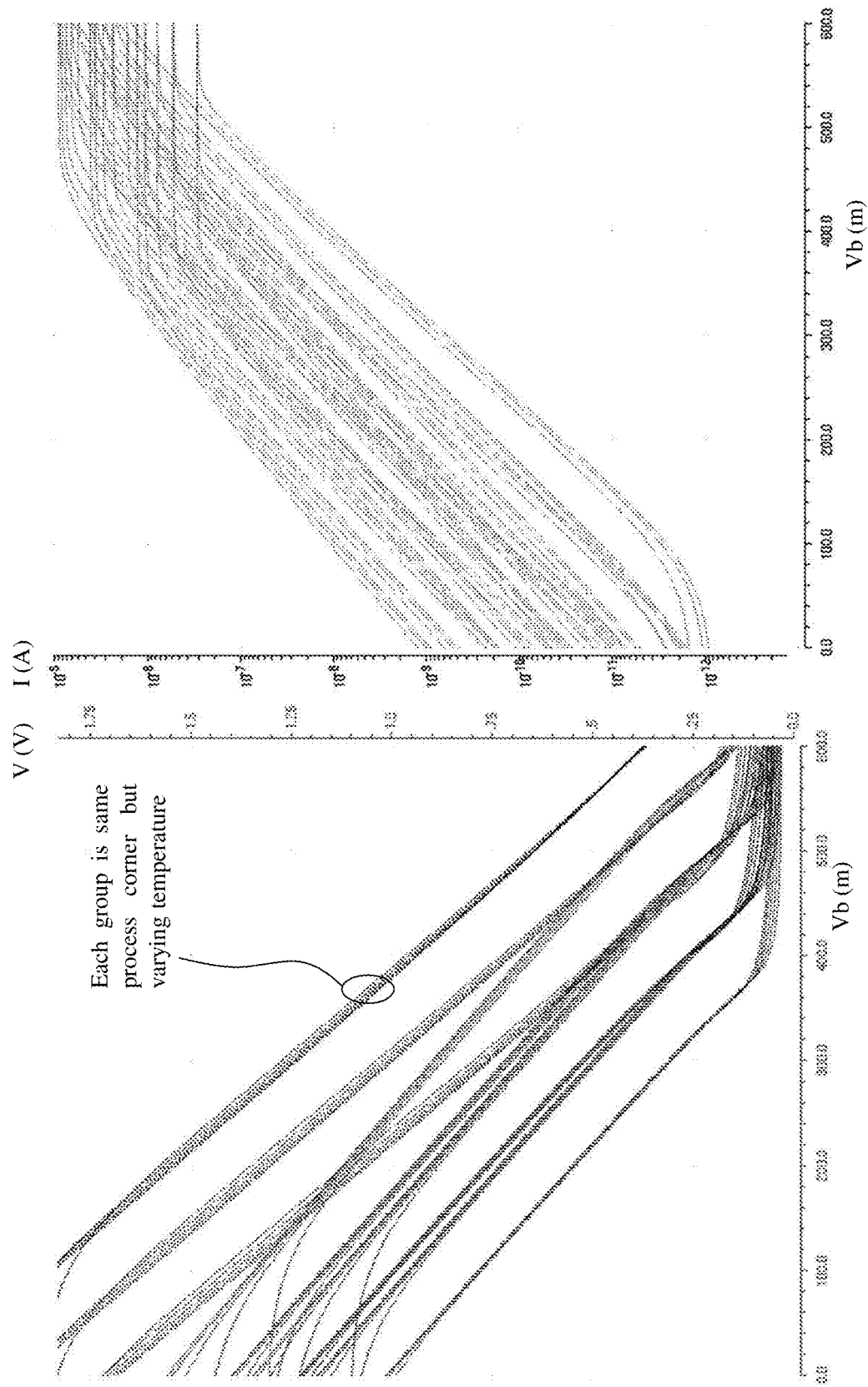
FIGS. 31 and 32 depict the DC response and DC analysis of the native/negative threshold MOSFET totem depicted in FIG. 30.

Accordingly, the inventors established the concept of a native transistor totem wherein instead of using one current branch for each "step-up" in voltage and since mutually non-overlapping minimal voltage drops are needed for each native transistor stepping up the voltage, they can be put in series and share the same current. The resulting voltage of the nodes is entirely dependant on the voltage threshold of the native transistors and the current source of the branch. Further, no external voltage reference or accurate voltage supply is required when $V_{ctrl}$=0V. This circuit is depicted in FIG. 30 whilst FIGS. 31 and 32 depict the DC response and DC analysis on $V_b$ respectively where $V_b$=$V_{ctrl}$.

Typical analog design issues to consider include:

transient operation stability: minimal capacitive decoupling is enough;

transient noise: ultra low due to being driven by transistor sources;

sensitivity to voltage supply variations (power supply rejection ratio, PSRR): which is prevented by the compounded cascode effect;

temperature variations: these are largely compensated with temperature effect acting in opposition to each and hence are mostly cancelled out;

process variations: these are not addressed with this approach and according require a design solution;

Component matching: which can be resolved in die layout; and

Component aging: which is not an issue as this arises with components under prolonged high voltage stress.

However, process variations are a fixed characteristic and never change throughout the life of an integrated circuit, this can be exploited to solve the process variations. An exemplary embodiment to solve the process variations issues is a resistor ladder with a supply dependent on the reference ladder itself. Such a circuit being depicted in FIG. 33. This provides several benefits including:
- covers a wide range of tuning due to the fact that the bottom transistor's current follows an exponential curve in function of the control voltage which is what is required;
- does not require factory calibration and can be automatically calibrated at start-up of the wireless radio incorporating the circuit;
- is independent to supply voltage;
- incorporates a negative feedback loop which reduces the remaining temperature induced variations further.

Figure 33:
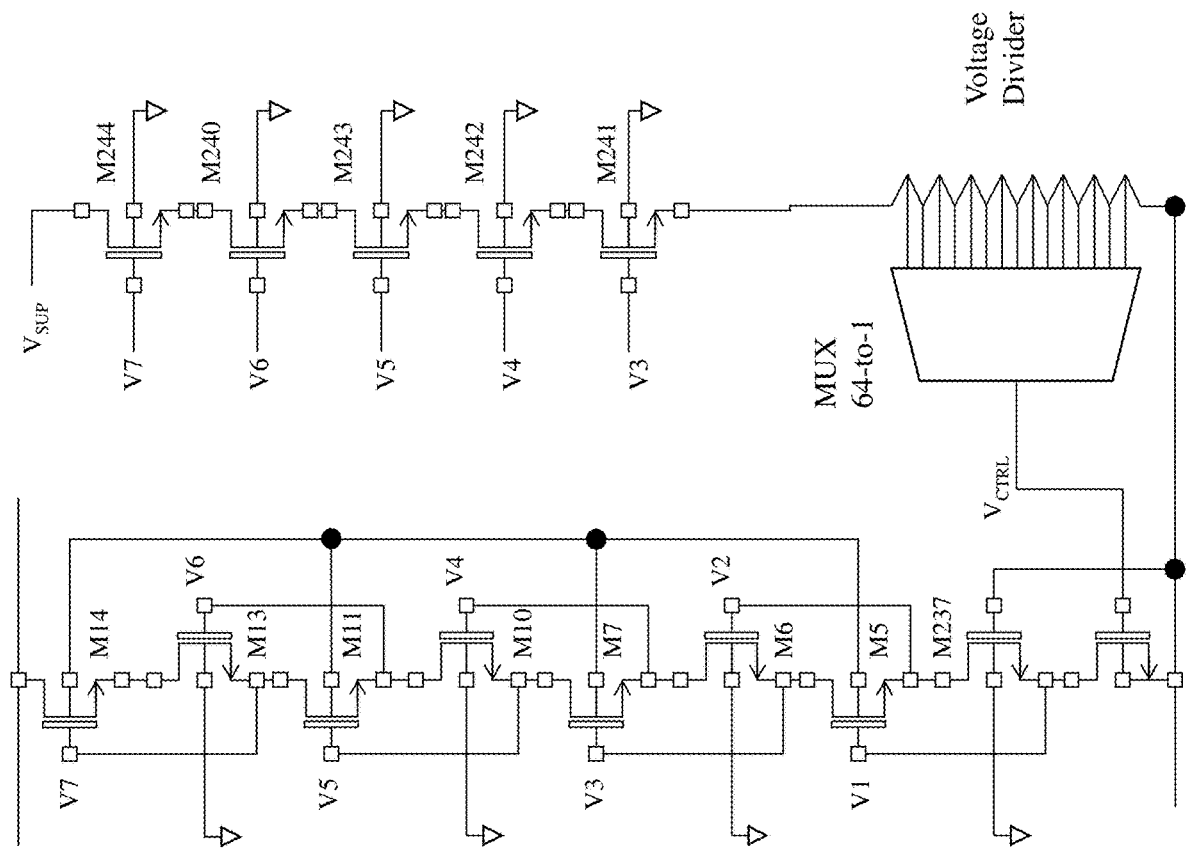
FIG. 33 depicts a resistor ladder with a supply dependent on the reference ladder in accordance with an embodiment of the invention.
Figure 35:
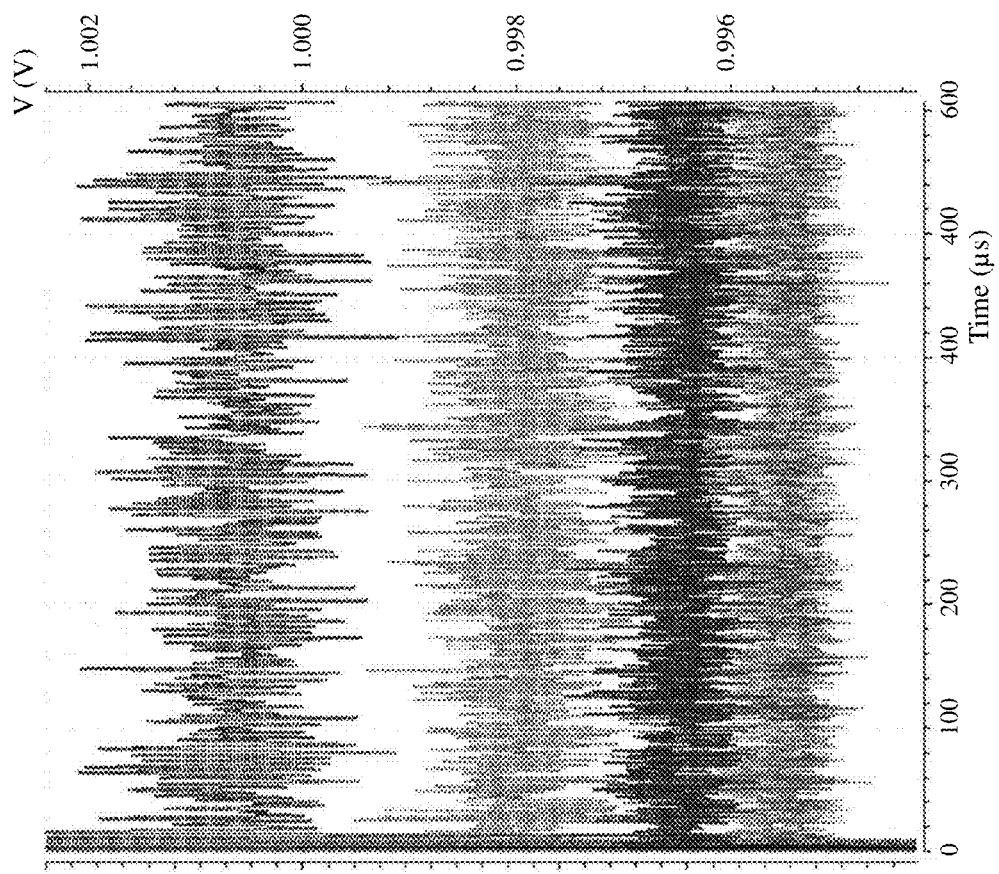
FIG. 35 depicts the transient noise performance for the exemplary native/negative MOSFET totem depicted in FIG. 33.
Figure 34:
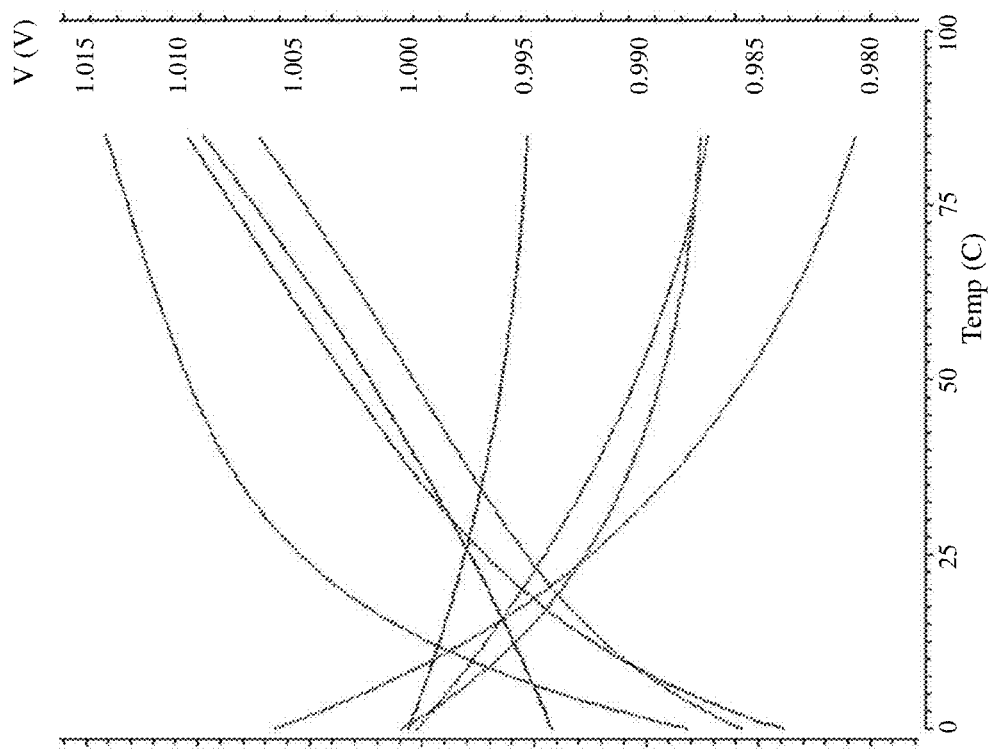
FIG. 34 depicts the reference voltage spread versus temperature for a native/negative threshold MOSFET totem according to an embodiment of the invention.

FIG. 34 depicts the reference voltage spread versus temperature for an exemplary native/negative MOSFET totem according to an embodiment of the invention as depicted in FIG. 33 whilst FIG. 35 depicts the transient noise performance for the exemplary native/negative MOSFET totem depicted in FIG. 33. Accordingly, compiled characteristics for the exemplary native/negative MOSFET totem depicted in FIG. 33 are:
- maximum voltage reference spread of ~26 mV/1 V;
- transient noise of ~1 mVpp typically and 2-3 mVpp at 85° C.;
- DC current consumption of 12 nA typical and maximum current<300 nA; and
- die area used with decoupling (excluding tuning branch) of ~11×~22

9. Ultra-Low Power Low Drop Out Regulator

Wireless radios according to embodiments of the invention as discussed above the UWB receiver, UWB transmitter and UWB transceiver circuits support aggressive duty-cycling in order to provide a very low-power design. In order to achieve such aggressive power reduction then the internal voltage converters such as the linear voltage reference buffers and the DC-DC converter should also be powered down to reach a sleep state power consumption below one microamp while still ensuring the SPI interface and all the important digital portion of the circuits remain supplied with power. Accordingly, these portions of the circuits that are always-on the digital circuitry is constrained to a very low leakage current (~100 nA) and thus has to be comprised of thick gate oxide input/output transistors. However, as the main operating voltage of the chip ranges from 1.8 V to 3.6 V then the digital transistors without voltage regulation have to be large thereby occupying significant die real estate and exhibiting excessive dynamic power consumption. Accordingly, the inventors have established an innovative feedback-less low dropout (LDO) regulator that does not have to perform significant voltage regulation but whose output voltage would be low enough and independent enough from the main chip supply that the transistors used for the always-on digital core are small enough.

Figure 36:
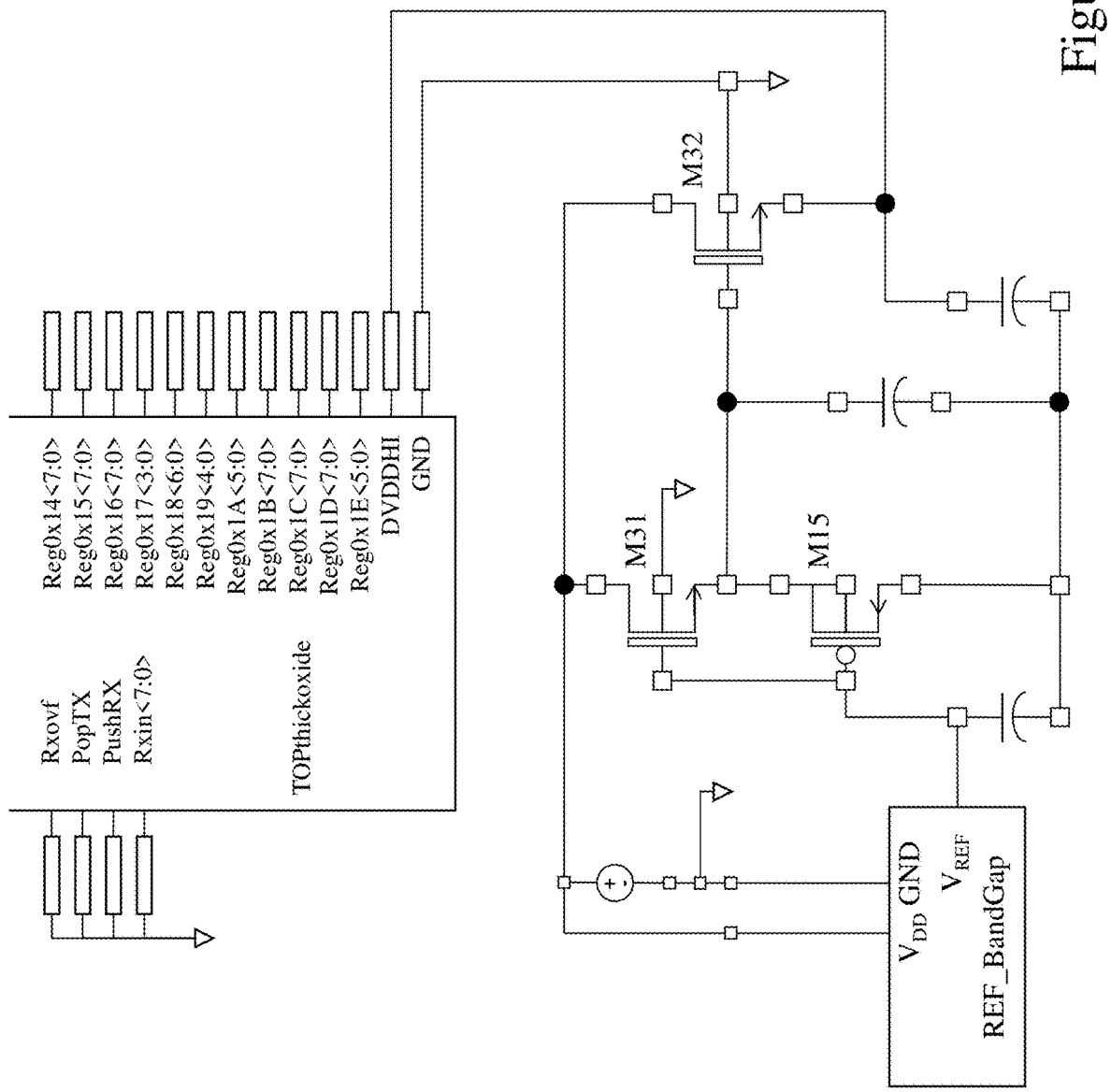
FIG. 36 depicts an exemplary schematic for an ultra-low power low drop out regulator according to an embodiment of the invention.

Further, a lower supply voltage reduces the extent of charge/discharge of all parasitic capacitance required for each digital signal to flip resulting in a much lower dynamic power consumption. Further, to actually save energy in total, the LDO should have a very low quiescent current (of the order of a few nanoamps) and accordingly it does not require or include feedback. Referring to the circuit depicted in FIG. 36 the output can vary by much more than a hundred millivolt depending on the operating condition, digital core clock rate and activity but because this is supplying only digital circuitry, the output voltage precision is not particularly significant for the proper operation of the circuit provided that it does not dip so low that the circuit becomes too slow. Within FIG. 36 the LDO is illustrated in context and constitutes of transistors M15, M31 and M32. As depicted, these are disposed between the reference bandgap circuit and the remainder of the digital circuit.

Accordingly, similarly to the biasless low power differential (exponential) transconductance stage described above in respect of Section 7 the first two transistors, M15 and M31, embody the equivalent of a CMOS class AB power amplifier which isolates the sensitive high-impedance node at the output of the bandgap from any digital noise that is fed through from the source of the large transistor M32 to its gate with the help of heavy capacitive decoupling (C28). Outside of this noise, there is no activity on the intermediate current branch of transistors M15 and M31, only a static current consumption, typically 3 nA. This is the only current preventing the LDO from being 100% current efficient but it isolates the sensitive input node and give a slight voltage increase from the bandgap output voltage of 1.3 volt due to the fact that the voltage threshold of the native NMOS M31 is much lower than the threshold of M15. In such a situation, the M32 transistor operates in either the sub-threshold or near threshold region where the transfer function from $V_{gs}$ to current is mostly exponential allowing for a variation of several orders of magnitude in current demand for one instant to another without resulting in a voltage drop, no more than a few hundred mV, although a circuit using the output is insensitive to it.

10. Dynamically Biased Pre-Amplifier with Latched Comparator

Figure 37A:
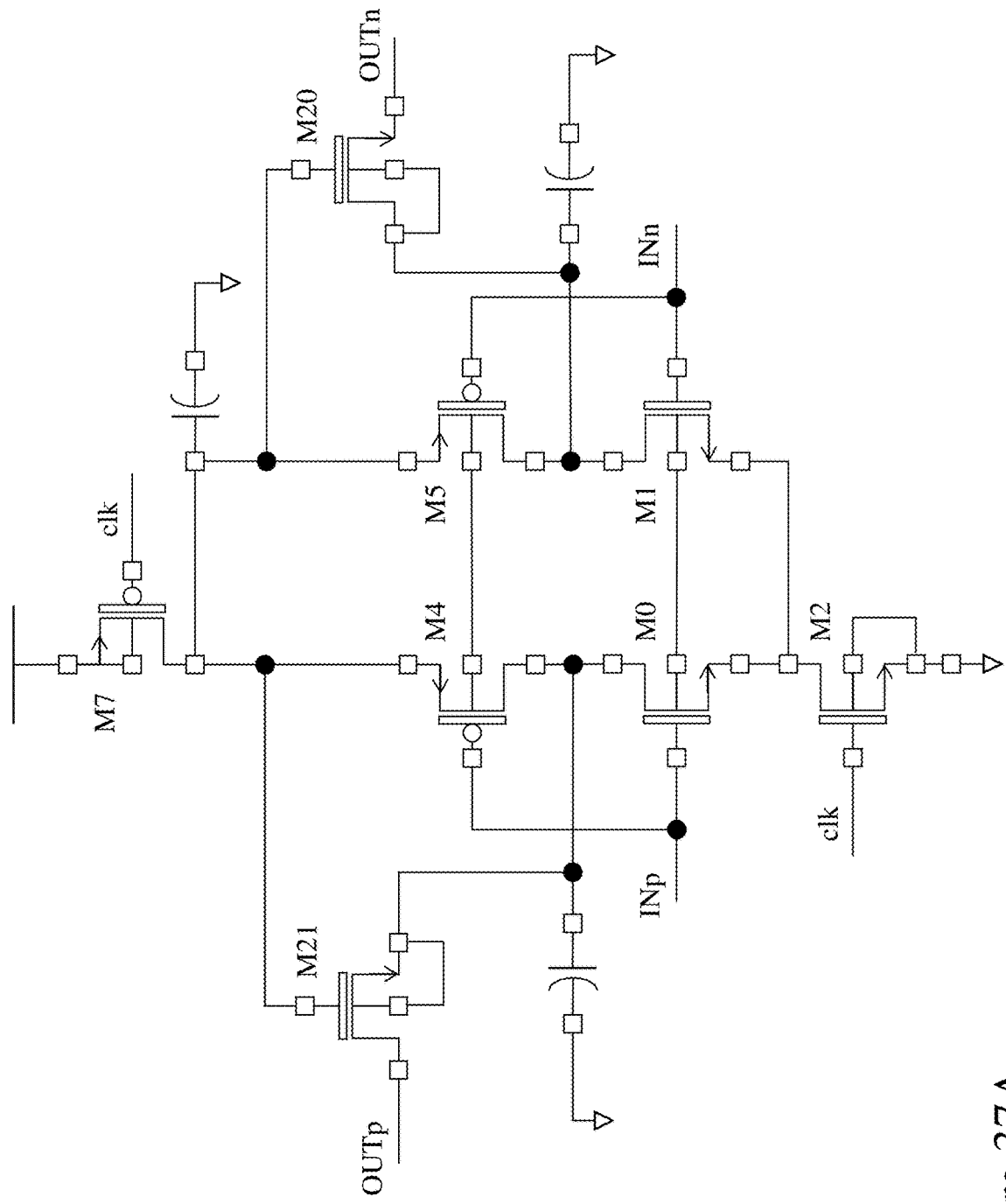
FIG. 37A depicts a self-contained dynamic comparator circuit according to an embodiment of the invention.
Figure 37B:
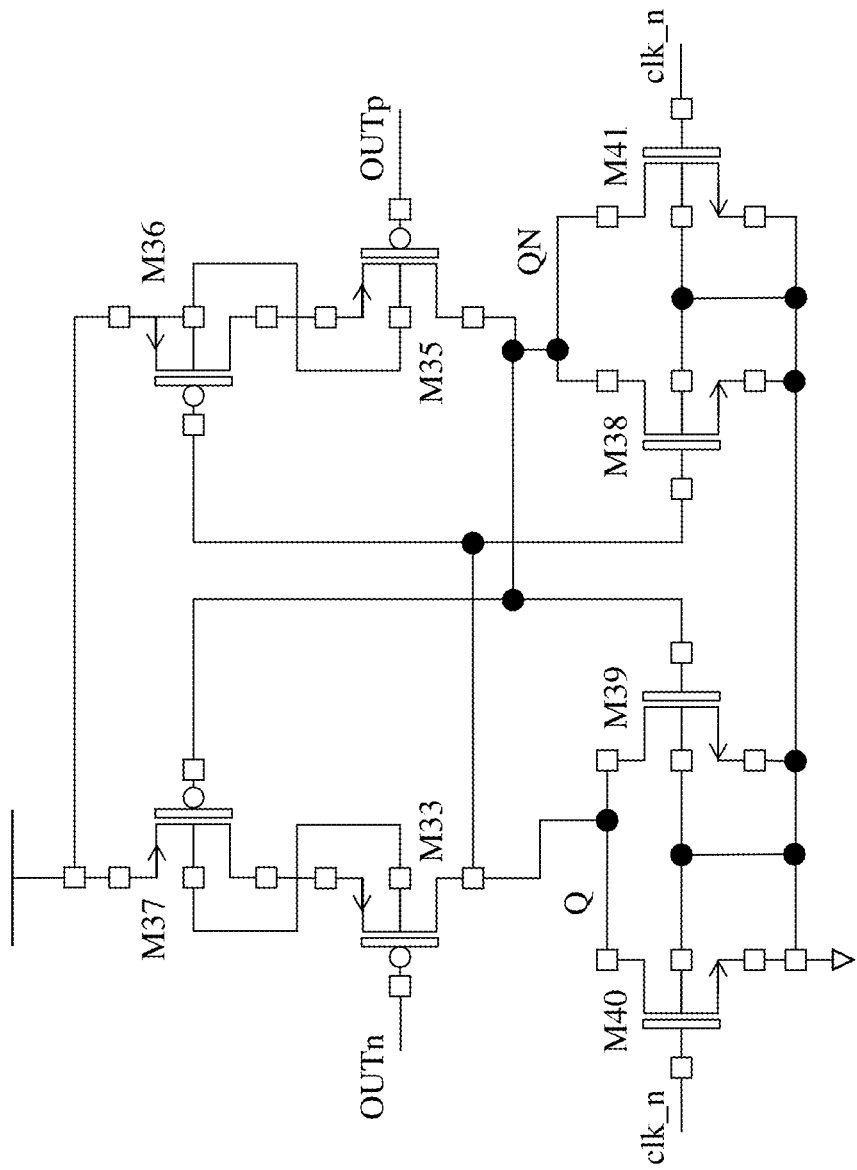
FIG. 37B depicts a regenerative latch to provide a context for the innovative ultra-low power low drop out regulator according to an embodiment of the invention.

The innovative circuit is depicted as a self-contained circuit within FIG. 37A where the regenerative latch depicted in FIG. 37B is presented solely to provide a context for the new innovative circuit and explain its function.

A consistent dilemma for circuit designers when designing a dynamic preamplification stage is the tradeoff between power consumption and accuracy. Due to the unavoidable sources of current noise in MOSFETs, especially thermal noise, there is significant current to sink through a differential pair of NMOS, PMOS (or both in this case) transistors to "average out" the current noise and provide an accurate comparison. However, the more current is sunk, the higher is the energy consumption.

Accordingly, it is beneficial to maximize the $g_m$ (transconductance factor) relative to the total current in the differential pair. Accordingly, referring to FIG. 37A this is addressed by providing both a NMOS and a PMOS input differential pair (namely M0/M1 and M4/M5 respectively) that together form something similar to current-starved inverters. Initially, the PMOS transistors were intended to be connected directly to VDD and made somewhat weaker than the NMOS transistors so that the output nodes would end-up being pulled low enough to turn on the input transistors of the latch (comprising M33 and M35). This results in a certain amount of static current wasted waiting for the regenerative latch to "make a decision" after the input PMOS transistors of the latch are turned on.

Accordingly, to address this and the need to adjust the strength (effective width) for various supply/reference voltages then a "dynamic bias" technique is implemented for the PMOS differential pair (M4/M5) instead of the NMOS differential pair (M0/M1). This results in an already limited amount of charge, and therefore less energy consumption, that is sunk unequally (by default) between the two PMOS transistors when the differential input voltage (INp−INn) is non-zero which helps to further amplify the difference between the pre-amplifier outputs. With this dynamic bias, as long as the PMOS transistors start stronger than the NMOS transistors, the voltage of nodes OUTp and OUTn will remain high until enough current have been sunk from the dynamic bias capacitor C10. When C10 gets drained enough and there isn't enough $V_{gs}$ to keep the PMOS transistors on stronger than the NMOS transistors, then the PMOS transistors change state from triode to saturation and the slightest voltage difference between the PMOS transistors will cause one of the PMOS to enter saturation slightly before the other one allowing the drain voltage to be pulled down a lot quicker. To further amplify the difference between the outputs, that drain (preamplifier output) voltage will be pulled down faster than its counterpart because a lower $V_{gs}$ for a PMOS means a higher $V_{gs}$ for the NMOS it is 'wrestling' current with since these share the same gate voltage. Accordingly, the fact that one node starts going down before the other and also is drained at a faster rate that its counterpart contributes to produce a comparator circuit which makes more accurate decisions.

Referring to FIG. 37A there is no explicit driving connection to nodes $n_{well}$ and $p_{well}$ because the option to connect it to any common voltage node or bias it then it would be evident that there are multiple options for achieving this which can be implemented in combination with the circuit of FIG. 37A. Furthermore, transistors M20 and M21 are optional provided that their drains are short-circuited with their respective sources before removing them and their only purpose are to prevent the OUTp and OUTn nodes from going down too far before the PMOS differential pair enters their saturation state (when $V_{ds}$ is roughly >100 mV) when the differential pair is actually effective at amplifying a differential signal. It would be evident to one skilled in the art that a pair of PMOS transistors required to recharge the nodes OUTp and OUTn to $V_{DD}$ after comparison are not depicted for clarity which should have their gates connected to the clock "clk" node.

Optionally within another embodiment of the invention the common source node for the PMOS transistors may be split into two separate nodes with two separate but equal capacitors. A benefit of this optional configuration is that since it's probably the NMOS transistors which are not dynamically bias that actually dictate how much current is sunk from each output node. In this manner, a greater output voltage difference or at least an equivalent one, can be achieved by separating the charges that have to be sunk between the two NMOS transistors so that the one that is sinking more current does not inadvertently sink more of the charge than is destined to be sunk by the other, slower NMOS. Accordingly, dumping more charges on the node that is supposed to drop in voltage before the other would be counterproductive.

Specific details are given in the above description to provide a thorough understanding of the embodiments. However, it is understood that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above and/or a combination thereof.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A method comprising:
   providing at least a DC-DC converter as part of an electronic circuit;
   establishing a sleep signal relating to powering down an electronic circuit into a sleep mode;
   turning off the DC-DC converter in dependence upon the establishment of the sleep signal;
   establishing a synthesized clock counter to count the number of synthesized clock cycles between the moment the sleep signal is raised and the moment the DC-DC converter is turned off;
   retaining the value of this synthesized clock counter during the sleep mode; and
   subtracting a time value established in dependence upon this retained synthesized clock counter value from a predetermined delay relating to when to wake the electronic circuit out of the sleep mode.

2. The method according to claim 1, wherein the DC-DC converter is turned-off upon a predetermined edge of a low frequency clock forming part of the electronic circuit.

3. The method according to claim 2, wherein the low frequency clock is at least one of operating at a frequency of 32 kHz and is generated by a crystal oscillator.

4. A method comprising:
   providing at least a DC-DC converter as part of an electronic circuit;
   providing a low frequency oscillator for generating a low frequency clock signal;
   providing a phase locked loop (PLL) which receives the low frequency clock signal and generates a high frequency PLL clock signal;

establishing a sleep signal relating to powering down an electronic circuit into a sleep mode where the sleep signal;

turning off the DC-DC converter in dependence upon the establishment of the sleep signal where the turning off of the DC-DC converter is synchronised to an edge of the low frequency clock signal;

establishing a synthesized clock counter to count the number of synthesized clock cycles between the moment the sleep signal is raised and the moment the DC-DC converter is turned off where the synthesized clock cycles are of the high frequency PLL clock signal;

retaining the value of this synthesized clock counter during the sleep mode within a sleep counter circuit forming part of the electronic circuit; and subtracting with the sleep counter circuit a time value established in dependence upon this retained synthesized clock counter value from a predetermined delay relating to when to turn on the DC-DC converter.

5. The method according to claim 4, further comprising turning on the DC-DC converter; wherein turning on the DC-DC converter is synchronized to another edge of the low frequency clock signal.

6. A method comprising:

establishing a synthesized clock counter to count the number of synthesized clock cycles between the moment a sleep signal is raised and the moment a DC-DC converter is turned off where the synthesized clock cycles are of a high frequency phase locked loop (PLL) clock signal generated by a PLL which receives a low frequency clock signal and generates the high frequency PLL clock signal and the sleep signal relates to powering down into a sleep mode an electronic circuit coupled to the DC-DC converter;

retaining the value of this synthesized clock counter during the sleep mode within a sleep counter circuit forming part of the electronic circuit; and subtracting with the sleep counter circuit a time value established in dependence upon this retained synthesized clock counter value from a predetermined delay relating to when to turn back on the DC-DC converter; wherein the synthesized clock cycles are of the high frequency PLL clock signal.

7. The method according to claim 6, wherein the DC-DC converter is turned off upon establishment of the sleep signal; and the turning off of the DC-DC converter is synchronized to an edge of the low frequency clock signal.

8. The method according to claim 6, further comprising turning on the DC-DC converter; wherein the turning on of the DC-DC converter is synchronised to another edge of the low frequency clock signal.

9. The method according to claim 6, wherein the low frequency clock is generated by a crystal oscillator.

* * * * *